US009498262B2

(12) United States Patent
Bankoski et al.

(10) Patent No.: US 9,498,262 B2
(45) Date of Patent: *Nov. 22, 2016

(54) MINIMALLY INVASIVE FIXATION SYSTEM

(75) Inventors: Brian R. Bankoski, West Grove, PA (US); Shaun Hanson, West Chester, PA (US); Ralph C. Solitario, Jr., Douglassville, PA (US); Caryn E. Bundra, Downingtown, PA (US); William N. Woodburn, Sr., Mantua, NJ (US); Mark Rossney, Downingtown, PA (US); Eric McDivitt, Schwenksville, PA (US); David Rathbun, Gap, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 42 days.

This patent is subject to a terminal disclaimer.

(21) Appl. No.: 12/828,884

(22) Filed: Jul. 1, 2010

(65) Prior Publication Data

US 2010/0268284 A1 Oct. 21, 2010

Related U.S. Application Data

(63) Continuation of application No. 11/734,201, filed on Apr. 11, 2007, now Pat. No. 7,758,584.

(60) Provisional application No. 60/791,503, filed on Apr. 11, 2006.

(51) Int. Cl.
*A61B 17/58* (2006.01)
*A61B 17/60* (2006.01)
(Continued)

(52) U.S. Cl.
CPC ........ *A61B 17/7082* (2013.01); *A61B 17/7076* (2013.01); *A61B 17/7079* (2013.01); *A61B 17/7083* (2013.01); *A61B 17/00234* (2013.01); *A61B 17/865* (2013.01)

(58) Field of Classification Search
CPC .......... A61B 17/7074; A61B 17/7076; A61B 17/7083; A61B 17/7085; A61B 17/7086; A61B 17/7091
USPC ....... 606/61, 86, 96, 99, 104, 246, 264–279, 606/300–321, 86 A
See application file for complete search history.

(56) References Cited

U.S. PATENT DOCUMENTS 2,250,417 A 7/1941 Ettinger
2,373,478 A 4/1945 Kuhn
(Continued)

FOREIGN PATENT DOCUMENTS

AU A-13672/95 3/1995 ......... 17/56
DE 9215561 1/1993
(Continued)

OTHER PUBLICATIONS

Kevin T. Foley, M.D., "CD Horizon® Sextant™: Rod Insertion System Surgical Technique," Medtronic Sofamor Danek (2002).
(Continued)

*Primary Examiner* — Ellen C Hammond
*Assistant Examiner* — Christina Negrellirodrigue
(74) *Attorney, Agent, or Firm* — Baker & Hostetler LLP

(57) ABSTRACT

A minimally invasive fixation system and method for providing access to a surgical site. The fixation system may include a holding assembly, the holding assembling preferably including a lateral implant holder which may be attached to a pedicle screw and a sleeve positioned in connection with the lateral implant holder to prevent the lateral implant holder from separating from the pedicle screw. The sleeve may further include a tissue protection portion to keep the tissue out of the surgical site. A holding sleeve may be operably connected to the holding assembly and pedicle screw and may be used to insert the pedicle screw into the body. Multiple constructs may be inserted into the body so that a portion of the holding assembly extends from the body and provides access to and visualization of the surgical site. A rod holder may also be used to insert a rod into the head of the screw. The rod may be held by the rod holder so that the rod may be angulated as the rod is inserted into the screw heads. Once the rod is positioned in the screw heads, locking caps and/or set screws may be positioned over the rod and engage the screw heads so that the position of the rod may be fixed with respect to the screws. In some embodiments, a movement mechanism may be used to move the screws relative to each other to compress and/or distract the vertebrae.

52 Claims, 26 Drawing Sheets

(51) Int. Cl.
*A61F 2/00* (2006.01)
*A61B 17/70* (2006.01)
*A61B 17/00* (2006.01)
*A61B 17/86* (2006.01)

(56) References Cited

U.S. PATENT DOCUMENTS

| | | |
|---|---|---|
| 3,575,405 A | 4/1971 | Harding |
| 3,604,487 A | 9/1971 | Gilbert et al. |
| 4,335,715 A | 6/1982 | Kirkley |
| 4,409,968 A | 10/1983 | Drummond |
| 4,411,259 A | 10/1983 | Drummond |
| 4,545,374 A | 10/1985 | Jacobson |
| 4,733,657 A | 3/1988 | Kluger |
| 4,817,587 A | 4/1989 | Janese |
| 4,827,918 A | 5/1989 | Olerud |
| 4,904,010 A | 2/1990 | Lacey et al. |
| 4,957,495 A | 9/1990 | Kluger |
| 5,015,247 A | 5/1991 | Michelson |
| 5,020,519 A | 6/1991 | Hayes et al. |
| 5,047,029 A | 9/1991 | Aebi et al. |
| D331,625 S | 12/1992 | Price et al. |
| 5,171,279 A | 12/1992 | Mathews |
| 5,207,678 A | 5/1993 | Harms et al. |
| 5,217,497 A | 6/1993 | Mehdian |
| 5,219,349 A | 6/1993 | Krag et al. |
| 5,242,443 A | 9/1993 | Kambin |
| 5,312,404 A | 5/1994 | Asher et al. |
| 5,344,422 A | 9/1994 | Frigg |
| 5,352,231 A | 10/1994 | Brumfield et al. |
| 5,360,431 A | 11/1994 | Puno et al. |
| 5,431,658 A | 7/1995 | Moskovich |
| 5,433,467 A | 7/1995 | Easterwood |
| 5,439,464 A | 8/1995 | Shapiro |
| 5,443,467 A | 8/1995 | Biedermann et al. |
| 5,474,555 A | 12/1995 | Puno et al. |
| 5,484,440 A | 1/1996 | Allard |
| 5,501,684 A | 3/1996 | Schlapfer et al. |
| 5,507,211 A | 4/1996 | Wagner |
| 5,520,690 A | 5/1996 | Errico et al. |
| 5,531,746 A | 7/1996 | Errico et al. |
| 5,562,661 A | 10/1996 | Yashimi et al. |
| 5,605,458 A | 2/1997 | Bailey et al. |
| 5,607,426 A | 3/1997 | Ralph et al. |
| 5,611,800 A | 3/1997 | Davis et al. |
| 5,613,968 A | 3/1997 | Lin |
| 5,624,441 A | 4/1997 | Sherman et al. |
| 5,624,442 A | 4/1997 | Mellinger et al. |
| 5,647,873 A | 7/1997 | Errico et al. |
| 5,649,931 A | 7/1997 | Bryant et al. |
| 5,667,506 A | 9/1997 | Sutterlin |
| 5,667,513 A | 9/1997 | Torrie et al. |
| 5,669,911 A | 9/1997 | Errico et al. |
| 5,676,664 A | 10/1997 | Allard et al. |
| 5,690,630 A | 11/1997 | Errico et al. |
| 5,707,371 A | 1/1998 | Metz-Stavenhagen |
| 5,720,751 A | 2/1998 | Jackson |
| 5,725,588 A | 3/1998 | Errico et al. |
| 5,728,046 A | 3/1998 | Mayer |
| 5,732,992 A | 3/1998 | Mauldin |
| 5,782,830 A | 7/1998 | Farris |
| 5,782,833 A | 7/1998 | Haider |
| 5,797,911 A | 8/1998 | Sherman et al. |
| 5,810,878 A | 9/1998 | Burel et al. |
| 5,817,094 A | 10/1998 | Errico et al. |
| 5,863,293 A | 1/1999 | Richelsoph |
| 5,876,402 A | 3/1999 | Errico et al. |
| 5,879,350 A | 3/1999 | Sherman et al. |
| 5,882,350 A | 3/1999 | Ralph et al. |
| 5,885,285 A | 3/1999 | Simonson |
| 5,885,286 A | 3/1999 | Sherman et al. |
| 5,888,204 A | 3/1999 | Ralph et al. |
| 5,910,141 A | 6/1999 | Morrison et al. |
| 5,928,139 A | 7/1999 | Koros et al. |
| 5,938,663 A | 8/1999 | Petreto |
| 5,946,988 A | 9/1999 | Metz-Stavenhagen |
| 5,951,559 A | 9/1999 | Burkhart |
| 5,964,760 A | 10/1999 | Richelsoph |
| 5,964,761 A | 10/1999 | Kambin |
| 5,991,997 A | 11/1999 | Schley et al. |
| 6,010,503 A | 1/2000 | Richelsoph et al. |
| 6,030,388 A | 2/2000 | Yoshimi et al. |
| 6,053,917 A | 4/2000 | Sherman et al. |
| 6,055,456 A | 4/2000 | Gerber |
| 6,066,174 A | 5/2000 | Farris |
| 6,074,391 A | 6/2000 | Metz-Stavenhagen et al. |
| 6,077,262 A | 6/2000 | Schlapfer et al. |
| 6,090,110 A | 7/2000 | Metz-Stavenhagen |
| 6,090,111 A | 7/2000 | Nichols |
| 6,090,113 A | 7/2000 | Le Couedic et al. |
| 6,132,432 A | 10/2000 | Richelsoph |
| 6,139,493 A | 10/2000 | Koros et al. |
| 6,139,549 A | 10/2000 | Keller |
| 6,149,653 A | 11/2000 | Deslauriers |
| 6,159,214 A | 12/2000 | Michelson |
| 6,183,472 B1 | 2/2001 | Lutz |
| 6,187,005 B1 | 2/2001 | Brace et al. |
| 6,189,422 B1 | 2/2001 | Stihl |
| 6,200,322 B1 | 3/2001 | Branch et al. |
| 6,206,826 B1 | 3/2001 | Mathews et al. |
| 6,214,006 B1 | 4/2001 | Metz-Stavenhagen |
| 6,224,598 B1 | 5/2001 | Jackson |
| 6,224,603 B1 | 5/2001 | Marino |
| 6,235,028 B1 | 5/2001 | Brumfield et al. |
| 6,251,112 B1 | 6/2001 | Jackson |
| 6,261,287 B1 | 7/2001 | Metz-Stavenhagen |
| 6,280,442 B1 | 8/2001 | Barker et al. |
| 6,302,410 B1 | 10/2001 | Wentworth et al. |
| 6,302,888 B1 | 10/2001 | Mellinger et al. |
| 6,355,040 B1 | 3/2002 | Richelsoph et al. |
| 6,360,750 B1 | 3/2002 | Gerber et al. |
| 6,361,535 B2 | 3/2002 | Jackson |
| RE37,665 E | 4/2002 | Ralph et al. |
| 6,368,321 B1 | 4/2002 | Jackson |
| 6,415,693 B1 | 7/2002 | Simon et al. |
| 6,440,113 B1 | 8/2002 | Brisebois et al. |
| 6,440,133 B1 | 8/2002 | Beale et al. |
| 6,475,218 B2 | 11/2002 | Gournay et al. |
| 6,485,491 B1 | 11/2002 | Farris et al. |
| 6,488,681 B2 | 12/2002 | Martin et al. |
| 6,488,682 B2 | 12/2002 | Kikuchi et al. |
| 6,512,958 B1 | 1/2003 | Swoyer et al. |
| 6,520,907 B1 | 2/2003 | Foley et al. |
| 6,530,926 B1 | 3/2003 | Davison |
| 6,530,929 B1 | 3/2003 | Justis et al. |
| 6,537,276 B2 | 3/2003 | Metz-Stavenhagen |
| 6,543,317 B1 | 4/2003 | Rinner et al. |
| 6,554,834 B1 | 4/2003 | Crozet et al. |
| 6,558,387 B2 | 5/2003 | Errico et al. |
| 6,565,565 B1 | 5/2003 | Yuan et al. |
| 6,579,291 B1 | 6/2003 | Keith et al. |
| 6,610,065 B1 | 8/2003 | Branch et al. |
| 6,613,091 B1 | 9/2003 | Zdeblick et al. |
| 6,626,347 B2 | 9/2003 | Ng |
| 6,626,905 B1 | 9/2003 | Schmiel et al. |
| 6,626,906 B1 | 9/2003 | Young |
| 6,648,888 B1 | 11/2003 | Shluzas |
| 6,660,004 B2 | 12/2003 | Barker et al. |
| 6,669,729 B2 | 12/2003 | Chin |
| 6,673,074 B2 | 1/2004 | Shluzas |
| 6,719,758 B2 | 4/2004 | Beger et al. |
| 6,726,692 B2 | 4/2004 | Bette |
| 6,736,816 B2 | 5/2004 | Ritland |
| 6,743,231 B1 | 6/2004 | Gray et al. |
| 6,780,186 B2 | 8/2004 | Errico et al. |
| 6,783,527 B2 | 8/2004 | Drewry et al. |
| 6,790,208 B2 | 9/2004 | Oribe et al. |
| 6,800,084 B2 | 10/2004 | Davison et al. |
| 6,821,277 B2 | 11/2004 | Teitelbaum |
| 6,827,722 B1 | 12/2004 | Schoenefeld |
| 6,843,791 B2 | 1/2005 | Serhan |
| 6,849,064 B2 | 2/2005 | Hamada |
| 6,929,606 B2 | 8/2005 | Ritland |
| 6,945,933 B2 | 9/2005 | Branch et al. |

(56) References Cited

U.S. PATENT DOCUMENTS

| | | |
|---|---|---|
| 7,008,422 B2 | 3/2006 | Foley et al. |
| 7,011,658 B2 | 3/2006 | Young |
| 7,011,660 B2 | 3/2006 | Sherman et al. |
| 7,018,379 B2 | 3/2006 | Drewry et al. |
| RE39,089 E | 5/2006 | Ralph et al. |
| 7,083,621 B2 | 8/2006 | Shaolian et al. |
| 7,104,992 B2 | 9/2006 | Bailey |
| 7,128,743 B2 | 10/2006 | Metz-Stavenhagen |
| 7,160,300 B2 | 1/2007 | Jackson |
| 7,166,109 B2 | 1/2007 | Biedermann et al. |
| 7,179,225 B2 | 2/2007 | Shluzas et al. |
| 7,179,261 B2 | 2/2007 | Sicvol et al. |
| 7,186,255 B2 | 3/2007 | Baynham et al. |
| 7,188,626 B2 | 3/2007 | Foley et al. |
| 7,250,052 B2 | 7/2007 | Landry et al. |
| 7,261,714 B2 | 8/2007 | Richelsoph |
| 7,282,064 B2 | 10/2007 | Chin |
| 7,303,562 B2 | 12/2007 | Cavagna et al. |
| 7,306,603 B2 | 12/2007 | Boehm, Jr. et al. |
| 7,371,239 B2 | 5/2008 | Dec et al. |
| 7,455,685 B2 | 11/2008 | Justis |
| 7,462,182 B2 | 12/2008 | Lim |
| 7,465,306 B2 * | 12/2008 | Pond et al. ............... 606/86 A |
| 7,470,279 B2 | 12/2008 | Jackson |
| 7,476,240 B2 * | 1/2009 | Raymond et al. ............ 606/279 |
| 7,491,207 B2 | 2/2009 | Keyer et al. |
| 7,491,208 B2 | 2/2009 | Pond, Jr. et al. |
| 7,491,218 B2 | 2/2009 | Landry et al. |
| 7,497,869 B2 * | 3/2009 | Justis ............... A61B 17/7002 606/279 |
| 7,520,879 B2 | 4/2009 | Justis et al. |
| 7,527,638 B2 | 5/2009 | Anderson et al. |
| 7,547,318 B2 | 6/2009 | Birkmeyer et al. |
| 7,563,264 B2 | 7/2009 | Landry et al. |
| 7,572,276 B2 | 8/2009 | Lim et al. ............... 606/246 |
| 7,597,694 B2 * | 10/2009 | Lim ............... A61B 17/7005 606/86 A |
| 7,608,081 B2 | 10/2009 | Abdelgany |
| 7,608,096 B2 | 10/2009 | Foley et al. |
| 7,618,424 B2 | 11/2009 | Wilcox et al. |
| 7,621,918 B2 | 11/2009 | Jackson |
| 7,651,502 B2 | 1/2010 | Jackson |
| 7,666,189 B2 | 2/2010 | Gerber et al. |
| 7,678,112 B2 | 3/2010 | Rezach |
| 7,686,809 B2 | 3/2010 | Triplett et al. |
| 7,691,132 B2 | 4/2010 | Landry et al. |
| 7,708,763 B2 | 5/2010 | Selover et al. |
| 7,717,944 B2 | 5/2010 | Foley et al. |
| 7,744,635 B2 | 6/2010 | Sweeney et al. |
| 7,758,584 B2 | 7/2010 | Bankoski et al. |
| 7,763,055 B2 | 7/2010 | Foley |
| 7,776,040 B2 | 8/2010 | Markworth et al. |
| 7,776,051 B2 | 8/2010 | Colleran et al. |
| 7,811,288 B2 | 10/2010 | Jones et al. |
| 7,815,664 B2 | 10/2010 | Sherman et al. |
| 7,824,411 B2 | 11/2010 | Varieur et al. |
| 7,824,413 B2 | 11/2010 | Varieru et al. |
| 7,842,044 B2 | 11/2010 | Runco et al. |
| 7,842,073 B2 | 11/2010 | Richelsoph et al. |
| 7,850,715 B2 | 12/2010 | Banouskou et al. |
| 7,850,716 B2 | 12/2010 | Taylor |
| 7,854,751 B2 | 12/2010 | Sicvol et al. |
| 7,862,587 B2 | 1/2011 | Jackson |
| 7,862,595 B2 | 1/2011 | Foley et al. |
| 7,867,259 B2 | 1/2011 | Foley et al. |
| 7,887,539 B2 | 2/2011 | Dunbar, Jr. et al. |
| 7,896,902 B2 | 3/2011 | Jeon et al. |
| 7,914,558 B2 | 3/2011 | Landry et al. |
| 7,918,792 B2 | 4/2011 | Drzyzga |
| 7,931,677 B2 | 4/2011 | Abdelgany |
| 7,955,355 B2 | 6/2011 | Chin et al. |
| 7,955,363 B2 | 6/2011 | Richelsoph |
| 7,976,569 B2 | 7/2011 | Justis |
| 7,985,242 B2 | 7/2011 | Forton et al. |
| 8,002,798 B2 | 8/2011 | Chin et al. |
| 8,021,398 B2 | 9/2011 | Sweeney et al. |
| 8,029,546 B2 | 10/2011 | Capote et al. |
| 8,034,084 B2 | 10/2011 | Landry et al. |
| 8,043,343 B2 | 10/2011 | Miller et al. |
| 8,066,739 B2 | 11/2011 | Jackson |
| 8,075,592 B2 | 12/2011 | Landry et al. |
| 8,088,152 B2 | 1/2012 | Schumacher |
| 8,092,494 B2 | 1/2012 | Butler et al. |
| 8,096,996 B2 | 1/2012 | Gutierrez et al. |
| 8,097,027 B2 | 1/2012 | Lim et al. |
| 8,100,828 B2 | 1/2012 | Frey et al. |
| 8,100,913 B2 | 1/2012 | Abdelgany |
| 8,100,915 B2 | 1/2012 | Jackson |
| 8,100,951 B2 | 1/2012 | Justis et al. |
| 8,105,361 B2 | 1/2012 | Anderson et al. |
| 8,118,737 B2 | 2/2012 | Perez-Cruet et al. |
| 8,123,751 B2 | 2/2012 | Shluzas |
| 8,128,665 B2 | 3/2012 | Banouskou et al. |
| 8,152,810 B2 | 4/2012 | Jackson |
| 8,172,855 B2 | 5/2012 | Abdou |
| 8,177,817 B2 | 5/2012 | Fallin |
| 8,262,662 B2 | 9/2012 | Beardsley et al. |
| 8,262,702 B2 | 9/2012 | Giger et al. |
| 8,287,546 B2 | 10/2012 | King et al. |
| 8,292,892 B2 | 10/2012 | Jackson |
| 8,357,184 B2 | 1/2013 | Woolley |
| 8,460,308 B2 | 6/2013 | Marino et al. |
| 8,469,960 B2 | 6/2013 | Hutton et al. |
| 8,480,713 B2 | 7/2013 | Rezach |
| 8,518,082 B2 | 8/2013 | Sicvol et al. |
| 8,535,318 B2 | 9/2013 | Peterson et al. |
| 8,585,741 B2 | 11/2013 | Gabelberger et al. |
| 8,679,129 B2 | 3/2014 | Sorrenti et al. |
| 2002/0020255 A1 | 2/2002 | Simon et al. |
| 2002/0107519 A1 | 8/2002 | Dixon et al. |
| 2002/0193802 A1 | 12/2002 | Zdeblick et al. |
| 2003/0040752 A1 | 2/2003 | Kitchens |
| 2003/0073998 A1 | 4/2003 | Pagliuca et al. |
| 2003/0115180 A1 | 6/2003 | Eves |
| 2003/0135220 A1 | 7/2003 | Cauthen |
| 2003/0149341 A1 | 8/2003 | Clifton |
| 2003/0149438 A1 | 8/2003 | Nichols et al. |
| 2003/0191371 A1 | 10/2003 | Smith et al. |
| 2003/0199872 A1 | 10/2003 | Markworth et al. |
| 2003/0208203 A1 | 11/2003 | Lim et al. |
| 2003/0216768 A1 | 11/2003 | Gitis et al. |
| 2003/0225408 A1 | 12/2003 | Nichols et al. |
| 2003/0236447 A1 | 12/2003 | Ritland |
| 2004/0002629 A1 | 1/2004 | Branch et al. |
| 2004/0024398 A1 | 2/2004 | Hovda et al. |
| 2004/0034351 A1 | 2/2004 | Sherman et al. |
| 2004/0039384 A1 | 2/2004 | Boehm, Jr. et al. |
| 2004/0092930 A1 | 5/2004 | Morrison |
| 2004/0138662 A1 | 7/2004 | Landry et al. |
| 2004/0143265 A1 | 7/2004 | Landry et al. |
| 2004/0147928 A1 | 7/2004 | Landry et al. |
| 2004/0147937 A1 | 7/2004 | Dunbar, Jr. et al. |
| 2004/0153068 A1 | 8/2004 | Janowski et al. |
| 2004/0172022 A1 | 9/2004 | Landry et al. |
| 2004/0176763 A1 | 9/2004 | Foley et al. |
| 2004/0215190 A1 | 10/2004 | Nguyen et al. |
| 2004/0254574 A1 | 12/2004 | Morrison et al. |
| 2004/0267275 A1 | 12/2004 | Cournoyer et al. |
| 2005/0004593 A1 | 1/2005 | Simonson |
| 2005/0010220 A1 | 1/2005 | Casutt et al. |
| 2005/0021031 A1 | 1/2005 | Foley et al. |
| 2005/0021040 A1 | 1/2005 | Bertagnoli |
| 2005/0038432 A1 | 2/2005 | Shaolian et al. |
| 2005/0065517 A1 | 3/2005 | Chin |
| 2005/0065518 A1 | 3/2005 | Michelson et al. |
| 2005/0070765 A1 | 3/2005 | Abdelgany et al. |
| 2005/0070901 A1 | 3/2005 | David |
| 2005/0075644 A1 * | 4/2005 | DiPoto et al. ............... 606/90 |
| 2005/0080418 A1 | 4/2005 | Simonson et al. |
| 2005/0085813 A1 | 4/2005 | Spitler et al. |
| 2005/0090824 A1 | 4/2005 | Shluzas et al. |
| 2005/0096654 A1 | 5/2005 | Lin |
| 2005/0131408 A1 | 6/2005 | Sicvol et al. |
| 2005/0131419 A1 | 6/2005 | McCord et al. |

(56) References Cited

U.S. PATENT DOCUMENTS

| | | |
|---|---|---|
| 2005/0131420 A1 | 6/2005 | Techiera et al. |
| 2005/0131421 A1 | 6/2005 | Anderson et al. |
| 2005/0131422 A1 | 6/2005 | Anderson et al. |
| 2005/0149036 A1 | 7/2005 | Varieur et al. |
| 2005/0149053 A1 | 7/2005 | Varieur et al. |
| 2005/0154389 A1 | 7/2005 | Selover et al. |
| 2005/0159650 A1 | 7/2005 | Raymond et al. |
| 2005/0171540 A1 | 8/2005 | Lim et al. |
| 2005/0182410 A1 | 8/2005 | Jackson |
| 2005/0192570 A1* | 9/2005 | Jackson .................. 606/61 |
| 2005/0192579 A1 | 9/2005 | Jackson |
| 2005/0192589 A1 | 9/2005 | Raymond et al. |
| 2005/0203532 A1 | 9/2005 | Ferguson et al. |
| 2005/0215999 A1 | 9/2005 | Birkmeyer et al. |
| 2005/0228380 A1 | 10/2005 | Moore et al. |
| 2005/0228382 A1 | 10/2005 | Richelsoph et al. |
| 2005/0228400 A1 | 10/2005 | Chao et al. |
| 2005/0234449 A1 | 10/2005 | Aferzon |
| 2005/0240181 A1 | 10/2005 | Boomer et al. |
| 2005/0277934 A1 | 12/2005 | Vardiman |
| 2006/0009780 A1 | 1/2006 | Foley et al. |
| 2006/0025768 A1 | 2/2006 | Iott et al. |
| 2006/0036244 A1 | 2/2006 | Spitler et al. |
| 2006/0036252 A1 | 2/2006 | Baynham et al. |
| 2006/0036255 A1 | 2/2006 | Pond, Jr. et al. |
| 2006/0036260 A1 | 2/2006 | Runco et al. |
| 2006/0069391 A1 | 3/2006 | Jackson |
| 2006/0074418 A1 | 4/2006 | Jackson |
| 2006/0074445 A1 | 4/2006 | Gerber et al. |
| 2006/0079894 A1 | 4/2006 | Colleran et al. |
| 2006/0079909 A1 | 4/2006 | Runco et al. |
| 2006/0084993 A1 | 4/2006 | Landry et al. |
| 2006/0095035 A1 | 5/2006 | Jones et al. |
| 2006/0106380 A1 | 5/2006 | Colleran et al. |
| 2006/0106394 A1 | 5/2006 | Colleran |
| 2006/0111712 A1 | 5/2006 | Jackson |
| 2006/0111713 A1 | 5/2006 | Jackson |
| 2006/0111714 A1 | 5/2006 | Foley et al. |
| 2006/0111715 A1 | 5/2006 | Jackson |
| 2006/0122597 A1 | 6/2006 | Jones et al. |
| 2006/0142716 A1 | 6/2006 | Long et al. |
| 2006/0142761 A1 | 6/2006 | Landry et al. |
| 2006/0167454 A1 | 7/2006 | Ludwig et al. |
| 2006/0173454 A1 | 8/2006 | Spitler et al. |
| 2006/0184172 A1 | 8/2006 | Michelson et al. |
| 2006/0184178 A1 | 8/2006 | Jackson |
| 2006/0200135 A1 | 9/2006 | Sherman et al. |
| 2006/0229614 A1 | 10/2006 | Foley et al. |
| 2006/0241596 A1 | 10/2006 | Rezach |
| 2006/0241649 A1 | 10/2006 | Vasta et al. |
| 2006/0247624 A1 | 11/2006 | Banouskou et al. |
| 2006/0247658 A1 | 11/2006 | Pond, Jr. et al. |
| 2006/0264942 A1 | 11/2006 | Lim et al. |
| 2006/0264962 A1 | 11/2006 | Chin et al. |
| 2006/0276803 A1 | 12/2006 | Salerni et al. |
| 2006/0293678 A1 | 12/2006 | Davison et al. |
| 2006/0293680 A1 | 12/2006 | Jackson |
| 2006/0293693 A1 | 12/2006 | Farr et al. |
| 2007/0016188 A1 | 1/2007 | Boehm, Jr. et al. |
| 2007/0016198 A1 | 1/2007 | Boehm, Jr. et al. |
| 2007/0016199 A1 | 1/2007 | Boehm, Jr. et al. |
| 2007/0016200 A1 | 1/2007 | Jackson |
| 2007/0025132 A1 | 2/2007 | Liaw |
| 2007/0032162 A1 | 2/2007 | Jackson |
| 2007/0073294 A1 | 3/2007 | Chin et al. |
| 2007/0083210 A1 | 4/2007 | Hestad |
| 2007/0106123 A1 | 5/2007 | Gorek et al. |
| 2007/0129731 A1 | 6/2007 | Sicvol et al. |
| 2007/0135817 A1 | 6/2007 | Ensign |
| 2007/0161987 A1 | 7/2007 | Capote et al. |
| 2007/0161998 A1 | 7/2007 | Whipple |
| 2007/0162046 A1 | 7/2007 | Vandewalle |
| 2007/0167946 A1 | 7/2007 | Triplett et al. |
| 2007/0167954 A1 | 7/2007 | Sicvol et al. |
| 2007/0173745 A1 | 7/2007 | Diederich et al. |
| 2007/0185491 A1 | 8/2007 | Foley et al. |
| 2007/0198015 A1 | 8/2007 | Foley et al. |
| 2007/0233067 A1 | 10/2007 | Taylor |
| 2007/0233079 A1 | 10/2007 | Fallin et al. |
| 2007/0238335 A1 | 10/2007 | Veldman et al. |
| 2007/0260125 A1 | 11/2007 | Strauss et al. |
| 2007/0270842 A1 | 11/2007 | Bankoski et al. |
| 2008/0009864 A1 | 1/2008 | Forton et al. |
| 2008/0039838 A1 | 2/2008 | Landry et al. |
| 2008/0045957 A1 | 2/2008 | Landry et al. |
| 2008/0051794 A1 | 2/2008 | Dec et al. |
| 2008/0051897 A1* | 2/2008 | Lopez et al. .................. 623/17.13 |
| 2008/0077139 A1 | 3/2008 | Landry et al. |
| 2008/0077155 A1 | 3/2008 | Diederich et al. |
| 2008/0081951 A1 | 4/2008 | Frasier et al. |
| 2008/0086132 A1 | 4/2008 | Biedermann et al. |
| 2008/0091213 A1 | 4/2008 | Jackson |
| 2008/0140132 A1 | 6/2008 | Perez-Cruet |
| 2008/0154278 A1 | 6/2008 | Abdelgany |
| 2008/0167688 A1 | 7/2008 | Fauth et al. |
| 2008/0177270 A1 | 7/2008 | Sorrenti et al. |
| 2008/0255567 A1 | 10/2008 | Accordino |
| 2008/0262318 A1 | 10/2008 | Gorek et al. |
| 2008/0288005 A1 | 11/2008 | Jackson |
| 2008/0294198 A1 | 11/2008 | Jackson |
| 2008/0294202 A1 | 11/2008 | Peterson et al. |
| 2008/0300638 A1 | 12/2008 | Beardsley et al. |
| 2009/0005814 A1 | 1/2009 | Miller et al. |
| 2009/0088604 A1 | 4/2009 | Lowry et al. |
| 2009/0093684 A1 | 4/2009 | Schorer |
| 2009/0138056 A1 | 5/2009 | Anderson et al. |
| 2009/0163924 A1 | 6/2009 | Justis |
| 2009/0171391 A1 | 7/2009 | Hutton et al. |
| 2009/0228052 A1 | 9/2009 | Beardsley et al. |
| 2009/0228055 A1 | 9/2009 | Jackson |
| 2009/0228056 A1 | 9/2009 | Jackson |
| 2009/0270916 A1 | 10/2009 | Ramsay et al. |
| 2009/0287253 A1 | 11/2009 | Felix et al. |
| 2009/0318972 A1 | 12/2009 | Jackson |
| 2010/0024487 A1 | 2/2010 | Khoo et al. |
| 2010/0030283 A1 | 2/2010 | King et al. |
| 2010/0036443 A1 | 2/2010 | Hutton et al. |
| 2010/0131016 A1 | 5/2010 | Gerber et al. |
| 2010/0174325 A1 | 7/2010 | Won et al. |
| 2010/0198272 A1 | 8/2010 | Keyer et al. |
| 2010/0268279 A1 | 10/2010 | Gabelberger et al. |
| 2010/0268284 A1 | 10/2010 | Bankoski et al. |
| 2010/0274252 A1 | 10/2010 | Bottomley et al. |
| 2010/0331849 A1 | 12/2010 | Riesinger et al. |
| 2011/0054537 A1 | 3/2011 | Miller et al. |
| 2011/0130634 A1 | 6/2011 | Solitario, Jr. et al. |
| 2011/0166606 A1 | 7/2011 | Stihl et al. |
| 2011/0184465 A1 | 7/2011 | Boehm |
| 2011/0184469 A1 | 7/2011 | Ballard et al. |
| 2011/0263945 A1 | 10/2011 | Peterson et al. |
| 2012/0089191 A1 | 4/2012 | Altarac et al. |
| 2012/0290012 A1 | 11/2012 | Rutledge |
| 2012/0303062 A1 | 11/2012 | Amstutz et al. |
| 2013/0253598 A1 | 9/2013 | Jackson |
| 2013/0274804 A1 | 10/2013 | Hutton et al. |
| 2014/0012321 A1 | 1/2014 | Hutton et al. |
| 2014/0074171 A1 | 3/2014 | Hutton et al. |
| 2014/0114360 A1 | 4/2014 | Gephart et al. |

FOREIGN PATENT DOCUMENTS

| | | |
|---|---|---|
| DE | 4238339 | 5/1994 |
| DE | 19726754 | 2/1999 |
| DE | 10027988 | 1/2002 |
| EP | 0528177 | 2/1993 |
| EP | 0558883 | 9/1993 |
| EP | 0483242 B1 | 5/1995 |
| EP | 0836835 | 4/1998 |
| EP | 0885598 | 12/1998 |
| EP | 0947174 | 10/1999 |
| EP | 0746255 B1 | 9/2002 |
| EP | 0981301 B1 | 8/2003 |

(56) References Cited

FOREIGN PATENT DOCUMENTS

| | | |
|---|---|---|
| EP | 0934027 B1 | 12/2003 |
| EP | 1392190 | 3/2004 |
| EP | 1087711 B1 | 5/2004 |
| EP | 0934028 B1 | 6/2004 |
| EP | 1459215 | 9/2004 |
| EP | 1214006 B1 | 10/2005 |
| EP | 1316295 B1 | 10/2005 |
| EP | 1119304 B1 | 12/2005 |
| EP | 1317215 B1 | 12/2005 |
| EP | 1642542 | 4/2006 |
| EP | 0986338 B1 | 7/2006 |
| EP | 1248573 B1 | 8/2006 |
| FR | 2 757 761 | 12/1996 ............ 17/88 |
| FR | 2757761 | 7/1998 |
| JP | 11076247 | 3/1999 ............ 17/2 |
| JP | 2004-512134 | 4/2004 |
| JP | 2004-516040 | 6/2004 |
| JP | 2012-501809 | 2/2012 |
| WO | WO 95/14437 | 6/1995 |
| WO | WO 02/36026 | 5/2002 |
| WO | WO 03/052634 | 6/2003 |
| WO | WO 2004/041100 | 5/2004 |
| WO | WO 2004/058082 | 7/2004 |
| WO | WO 2005/058141 | 6/2005 |
| WO | WO 2005/060534 | 7/2005 |
| WO | WO 2006/042188 | 4/2006 |
| WO | WO 2006/060430 | 6/2006 |
| WO | WO 2006/116305 | 11/2006 |
| WO | WO 2006/116662 | 11/2006 |
| WO | WO 2007/022790 | 3/2007 |
| WO | WO 2007/025132 | 3/2007 |
| WO | WO 2007/038350 | 4/2007 |
| WO | WO 2007/067443 | 6/2007 |
| WO | WO 2007/070757 | 6/2007 |
| WO | WO 2007/117366 | 10/2007 |
| WO | WO 2008/014477 | 1/2008 |
| WO | WO 2008/022268 | 2/2008 |
| WO | WO 2009/011929 | 1/2009 |
| WO | WO 2009/055026 | 4/2009 |
| WO | WO 2010/030916 | 3/2010 |

OTHER PUBLICATIONS

Charles L. Branch, Jr., M.D., Kevin T. Foley, M.D., "Tangent™: Posterior Impacted Instrument Set Technique," Medtronic Sofamor Danek (2002).

Donald L. Hilton, Jr., M.D., Sylvain Palmer, M.D., "METR$_x$: Microdiscectomy Surgical Technique" Medtronic Sofamor Danek (2001).

Atavi™: Atraumatic Spine Fusion System—Endoscopic Posterolateral Fusion, Endius (2001).

Aperture™ Spinal Access System, DePuy AcroMed (2003).

Thongtrangan, M.D., et al., "Minimally invasive spinal surgery: a historical perspective"; Neurosurg Focus 16 (1):Article 13, 2004.

Müller, M.D., et al., "A Keyhole Approach for Endoscopically Assisted Pedicle Screw Fixation in Lumbar Spine Instability", Neurosurgery, vol. 47, No. 1, Jul. 2000.

Turner, M.D., "A New, Radially Expanding Access System for Laparoscopic Procedures versus Conventional Cannulas", The Journal of the American Association of Gynecologic Laparoscopists, vol. 3, No. 4, Aug. 1996.

Kambin, M.D., "The Role of Minimally Invasive Surgery in Spinal Disorders", Advances in Operative Orthopaedics, vol. 3, 1995.

Stryker Spine, Technique Guide, XIA SinalSytem, dated 1999.

DePuy Acromed, Technique Guide, Moss Miami System, dated 1999.

Harms, "Polyaxial Reduction Screw: Surgical Technique", Depuy AcroMed, 1998, 13 pages.

International Patent Application No. PCT/US2007/066469: International Search Report dated Aug. 1, 2008, 6 pages.

Muller et al., "Techniques and Applications : A Keyhole Approach for Endoscopically assisted Pedicle Screw Fixation in Lumbar Spine Inability", Jul. 2000 Neurosurgery, 47(1), 11 pages.

Synthes Spine, "Constellation CP System: A Minimally Invasive System for use with Cannulated Pangea", Technique Guide, Synthes Spinem, 2008, 41 pages.

Wiltse et al., "New Uses and Refinements of the Paraspinal Approach to the Lumbar Spine" Jan. 18, 1988, 22 pages.

Matrix Spine System—Deformity Technique Guide, "A Posterior Pedicle Screw, Hook, and Rod Fixation System," Synthes, © Aug. 2010, 75 pages.

\* cited by examiner

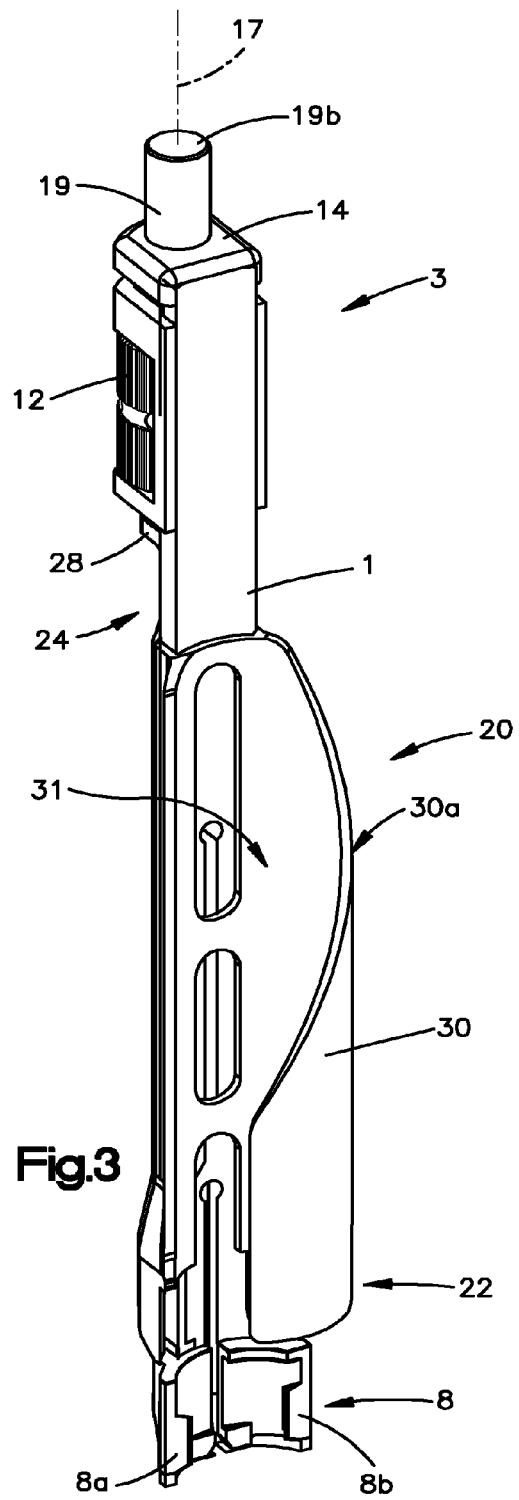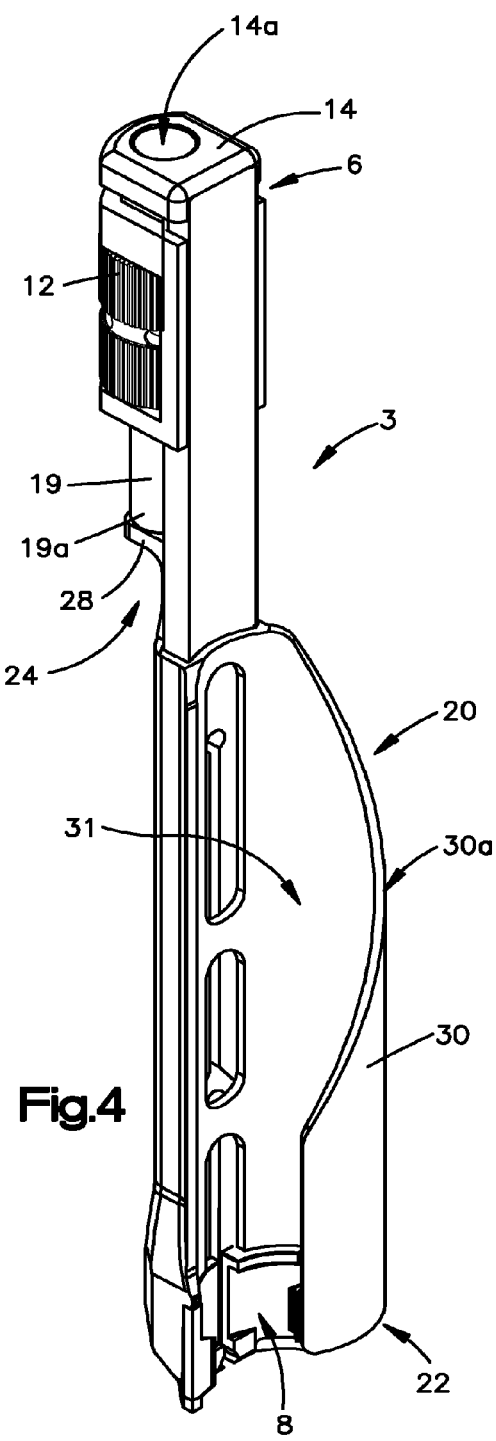

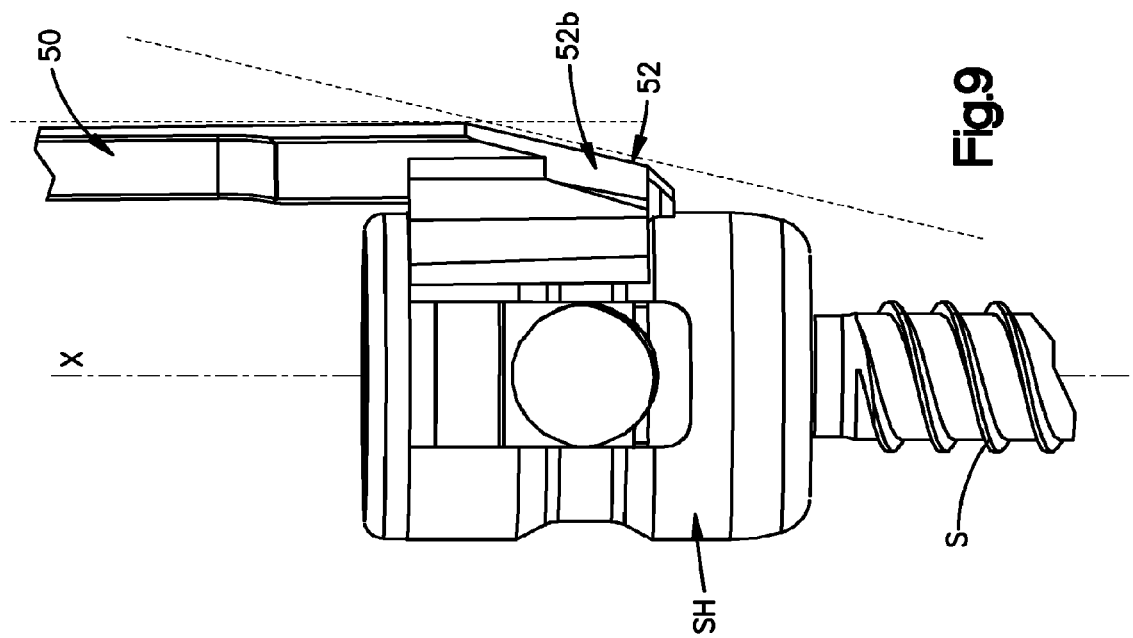
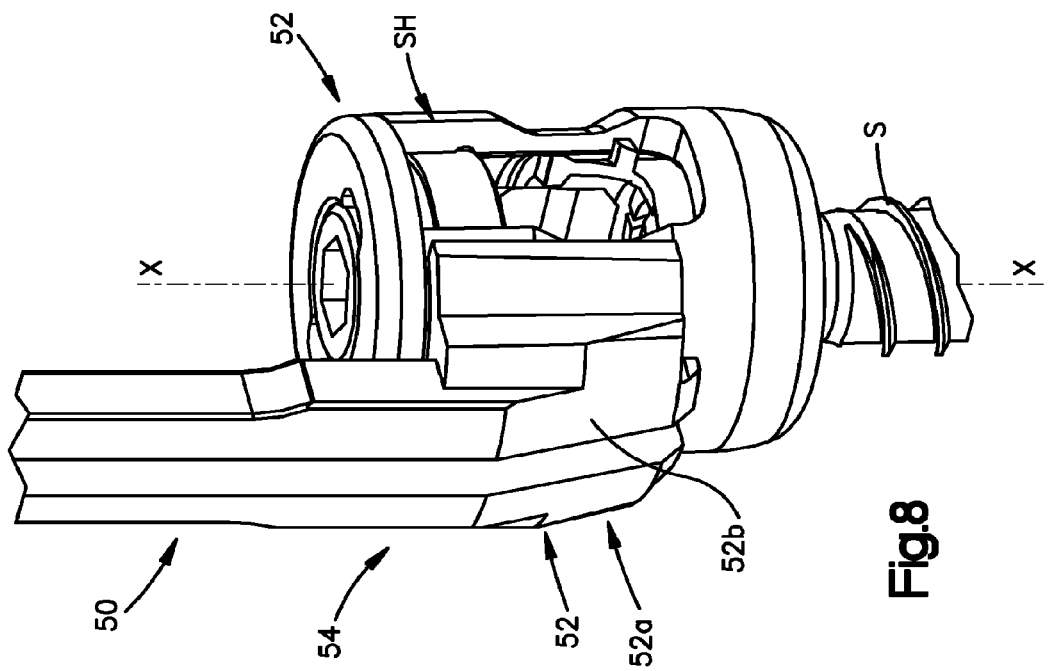

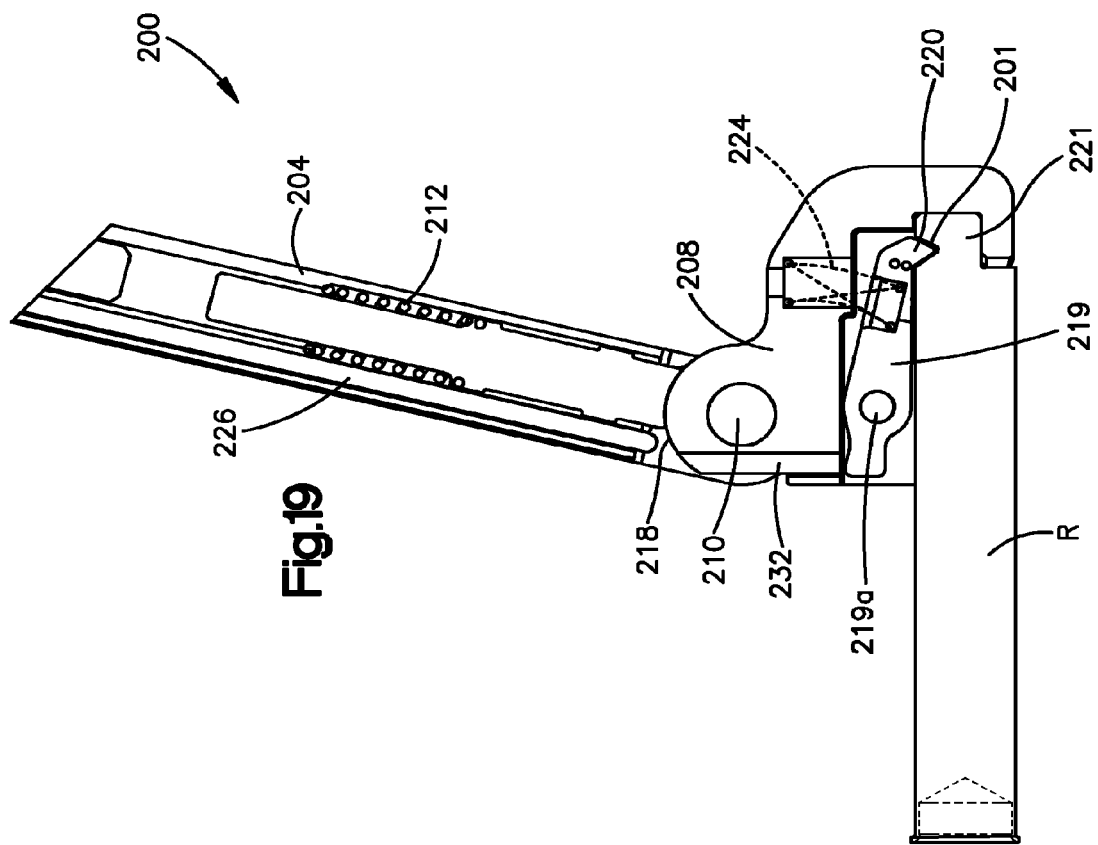

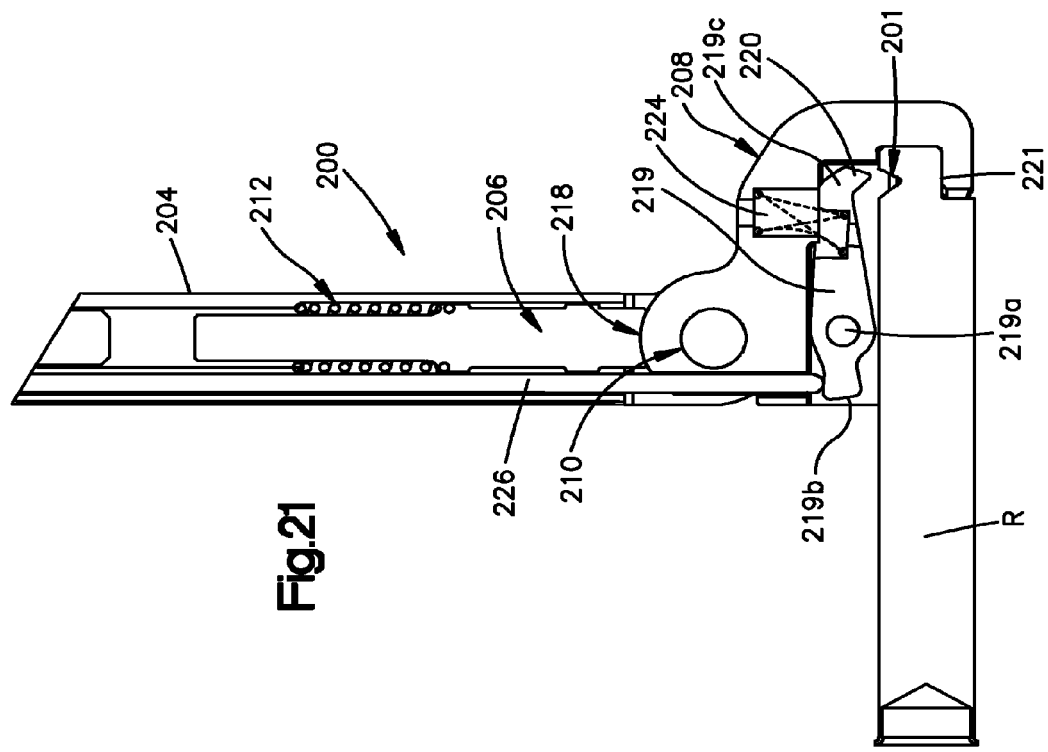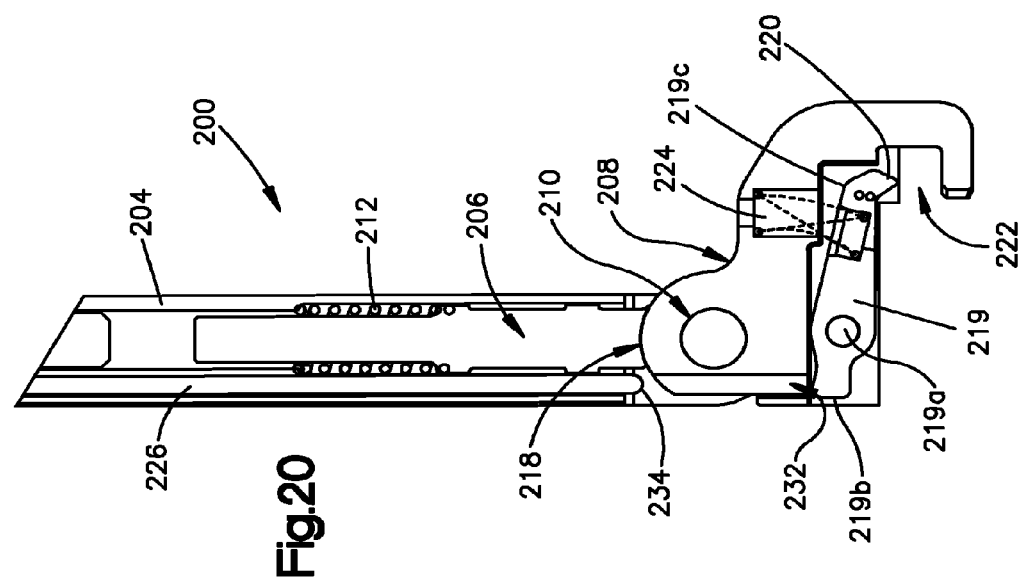

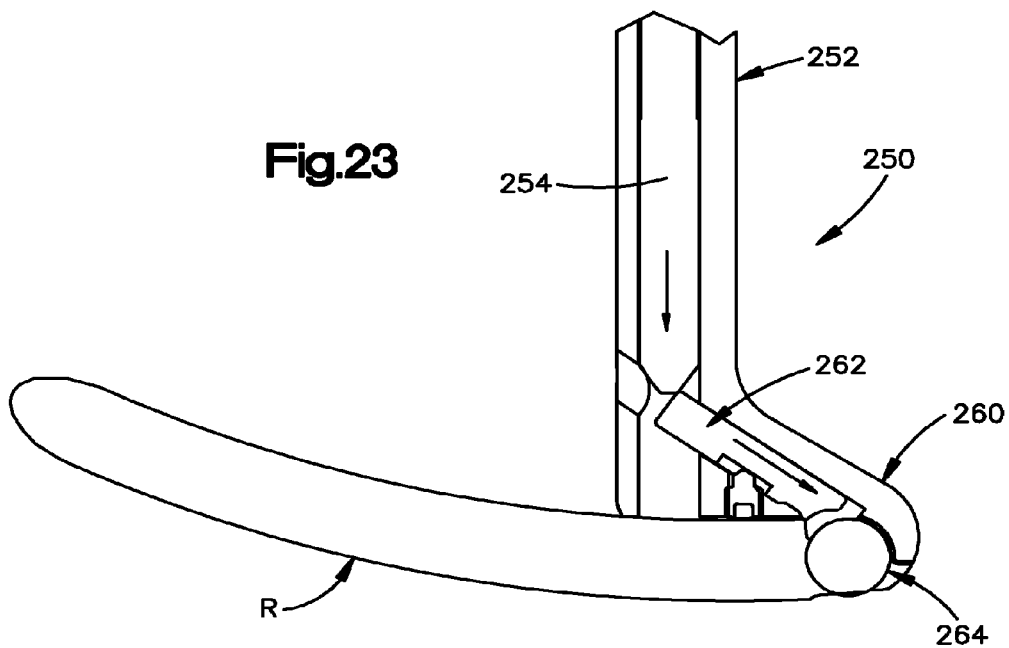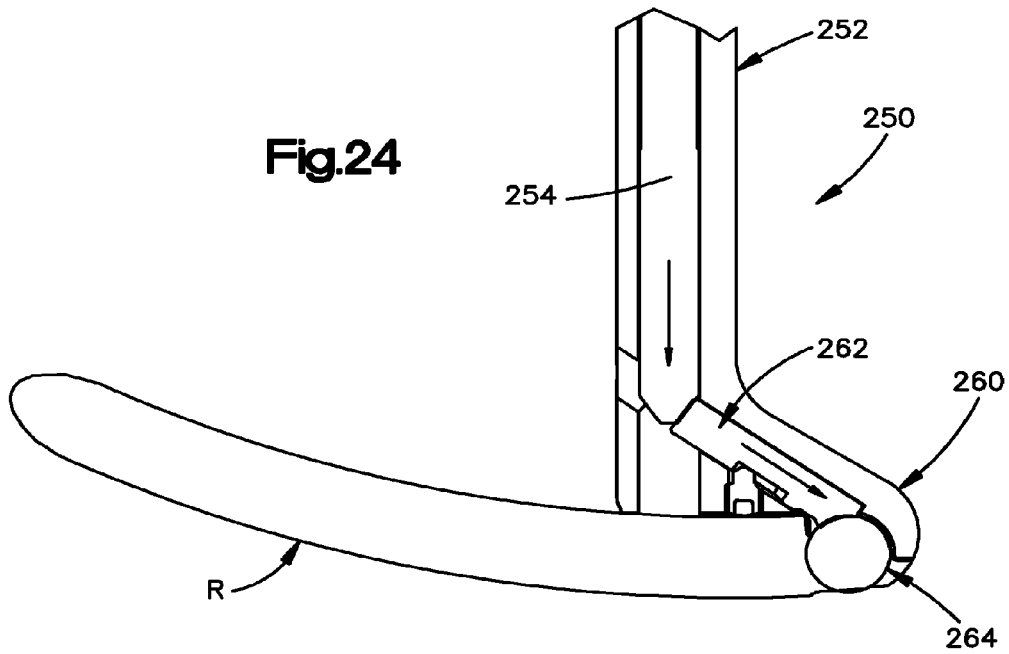

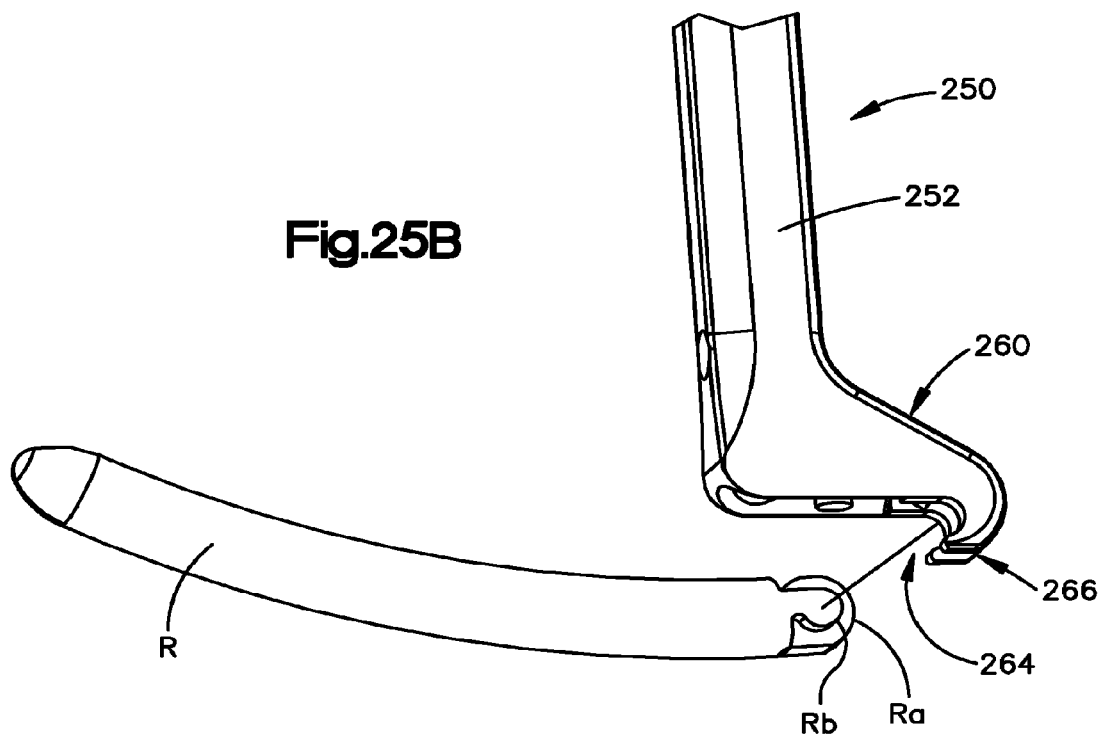
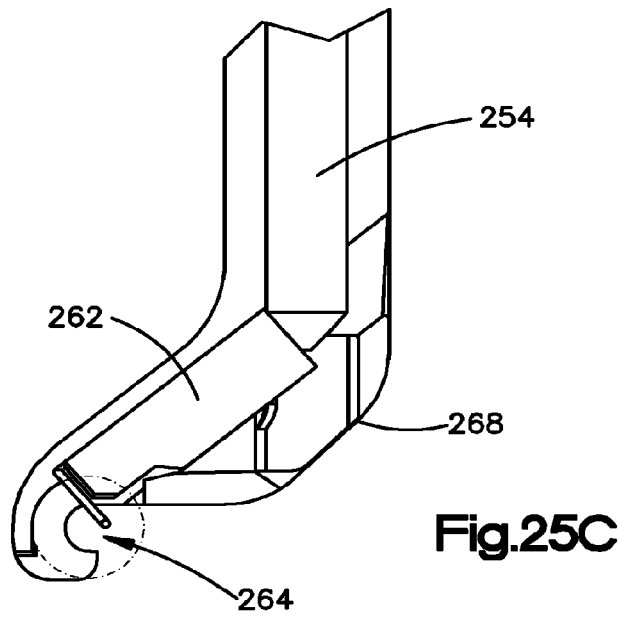

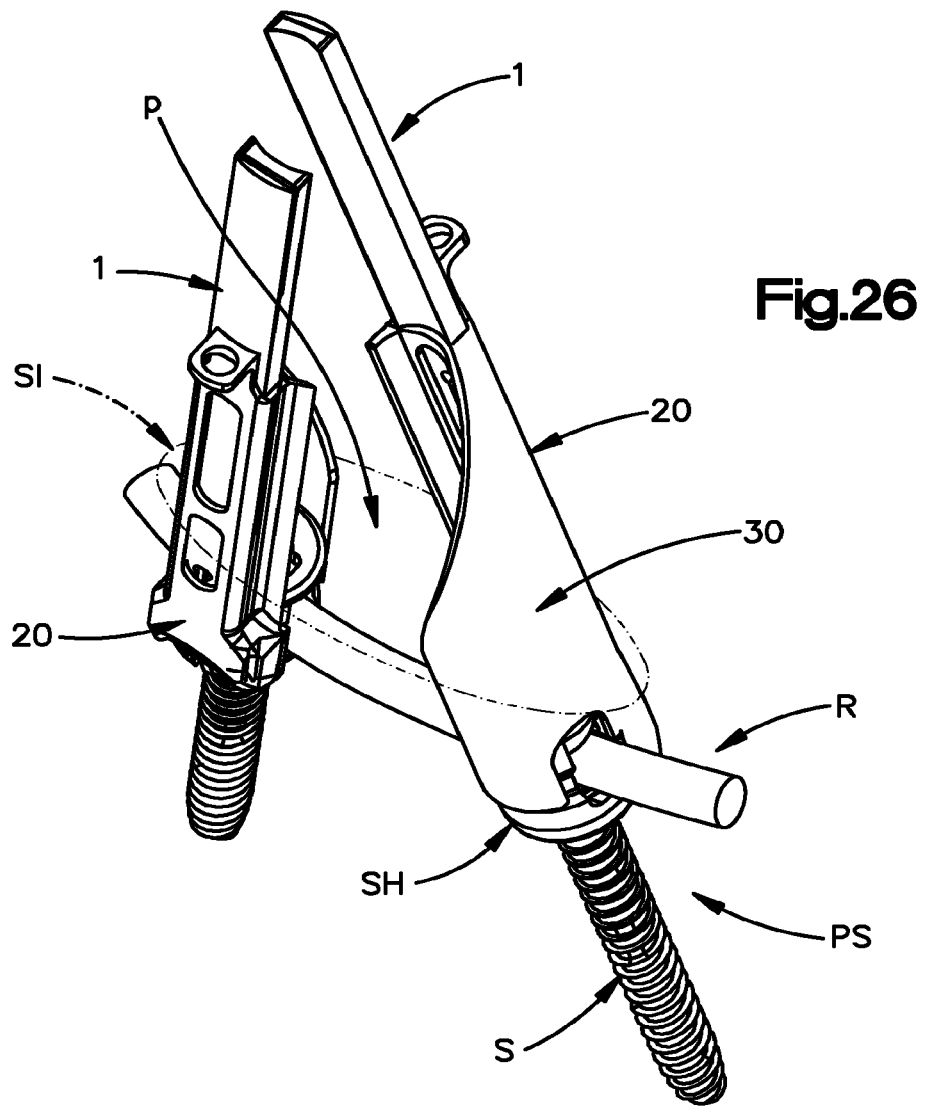

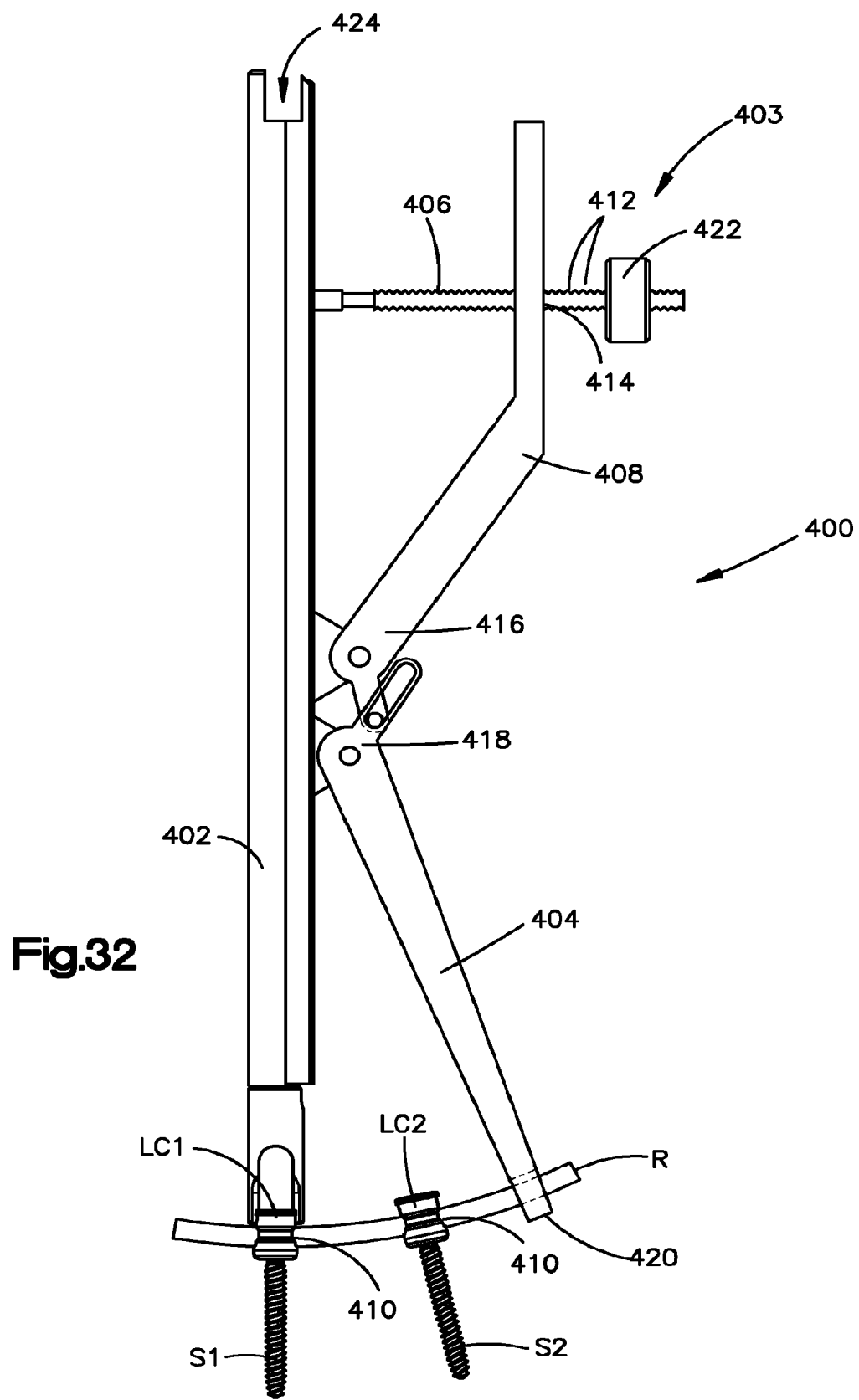

MINIMALLY INVASIVE FIXATION SYSTEM

CROSS REFERENCE TO RELATED APPLICATION

This application is a continuation application of U.S. patent application Ser. No. 11/734,201 filed Apr. 11, 2007, now U.S. Pat. No. 7,758,584 which claims the benefit of U.S. Provisional Application No. 60/791,503 filed Apr. 11, 2006, the entire content of which are expressly incorporated herein by reference thereto.

FIELD OF THE INVENTION

The fixation system relates to a system for performing a less or minimally invasive surgery and, in particular, to a system for creating a passageway or access pathway or portal into a patient's body, preferably in the patient's spine and, preferably from a posterior direction for implanting a spinal fixation system to stabilize the patient's spine.

BACKGROUND OF THE INVENTION

It is known in the art to use retractors and/or cannulas to provide a surgeon with an access portal to a surgical site in a patient's body. In particular, retractors and/or cannulas may be used to perform spinal operations, for example, discectomies, laminectomies, facectomies, pedicle screw fixation, etc., such as in minimally invasive procedures.

Known minimally invasive fixation systems have certain drawbacks. For example, retractors generally cause more trauma to the body than expandable cannulas since retractors tend to stretch tissue from the skin down to the surgical site.

While using cannulas (i.e., expandable cannulas, fixed diameter cannulas, etc.) may reduce trauma to the body as compared to retractors, for many surgical procedures, a surgeon must use a number of cannulas positioned adjacent to one another. A major drawback of using multiple cannulas is that if the surgeon needs to reposition adjacent cannulas, the cannulas may interfere with one another.

Thus, it is desirable to have a minimally invasive fixation system which provides a surgeon with increased ability to move and manipulate surgical instrumentation and implants into and within the body as well as an increased ability to visualize a surgical site while, at the same time, causing reduced amounts of trauma to the body. It is also desirable to provide a system which may be used to guide instrumentation into the body and may be configured so that parts of the system do not interfere with each other.

SUMMARY OF THE INVENTION

The fixation system relates to a minimally invasive surgical system, for example, for securing screws into or to bone or tissue(s) of a patient's body. An embodiment of the system, for example, includes one or more bone anchors, for example, pedicle screws, sized and configured to be selectively inserted into a bone tissue; a holding assembly associated with each bone anchor, the holding assembly may include a lateral implant holder and a sleeve. The lateral implant holder preferably includes a distal end constructed and arranged to selectively receive one of the bone anchors. The sleeve may include a distal end, a first tissue protection portion and preferably is constructed and arranged to associate with, couple to or selectively receive the lateral implant holder. Preferably, the tissue protection portion is sized and configured so that the tissue protection portion of adjacent holding assemblies do not interfere with each other when inserted into the body.

Another embodiment of the system includes a pedicle screw having a screw head, a lateral implant holder having a plurality of jaw members for retaining the screw head, and a sleeve moveable relative to the lateral implant holder. Preferably, the sleeve is sized and configured to prevent the lateral implant holder from separating from the screw head when the distal end of the sleeve is positioned over the plurality of jaw members of the lateral implant holder.

An embodiment of a method for implanting a rod into a rod-receiving channel formed in the screw heads of the pedicle screws include attaching the screw to a lateral implant holder and moving the sleeve to retain the screw in the engagement portion formed at the distal end of the lateral implant holder. The lateral implant holder, screw and sleeve may be inserted into the body through an incision made in the patient's skin. Each sleeve preferably includes a tissue protection portion extending out from the body, the tissue protection portion being sized and configured to reduce the amount of interference with adjacent tissue protection portions. A driving mechanism may also be used to insert the screw into the bone, and the rod may be inserted through the incision and into the rod receiving channel formed in the screw head. Preferably, the rod is inserted into the body at a first position and is moved into a second position different from the first position as the rod is inserted into the screw head.

The system may comprise the features of construction, combination of elements, and arrangement of parts which will be exemplified in the construction hereinafter set forth, but the scope of the invention should not be limited to such features, combination of elements or arrangement of parts.

The invention accordingly comprises the several elements and the relation of one or more of such elements with respect to each of the others, and the apparatus embodying features of construction, combination (s) of elements and arrangement of parts which are adapted to effect such steps, all as exemplified in the following detailed disclosure, and the scope of the invention will be indicated in the claims.

BRIEF DESCRIPTION OF THE INVENTION

The system is explained in even greater detail in the following exemplary drawings. The drawings are merely exemplary to illustrate the structure of preferred devices and certain features that may be used singularly or in combination with other features. The invention should not be limited to the embodiments shown.

FIG. 3 is a perspective view of the lateral implant holder of FIG. 1 with the sleeve of FIG. 2 attached in a first position thereto;

FIG. 4 is a perspective view of the lateral implant holder of FIG. 1 with the sleeve of FIG. 2 attached in a second position thereto;

FIG. 8 is a perspective view of an alternative lateral implant holder engaging a screw;

FIG. 9 is a side view of the construct of FIG. 8;

FIG. 19 is a cross-sectional view of an embodiment of a rod holder;

FIG. 20 is a cross-sectional view of a portion of the rod holder of FIG. 18 in a first position;

FIG. 21 is a cross-sectional view of a portion of the rod holder of FIG. 18 in a second position;

FIG. 23 is a cross-sectional view of a portion of the rod holder of FIG. 23 in a first position;

FIG. 24 is a cross-sectional view of a portion of the rod holder of FIG. 23 in a second position;

FIG. 25B is a side view of a portion of the rod holder of FIG. 25A and a rod;

FIG. 25C is a side cross-sectional view of a portion of the rod holder of FIG. 25A;

FIG. 26 is a perspective view of an embodiment of an assembly having two devices each attached to a pedicle screw and a rod spanning between the two pedicle screws;

FIG. 32 is a perspective view of an alternative embodiment of a compressor assembly.

DETAILED DESCRIPTION

Figure 1:
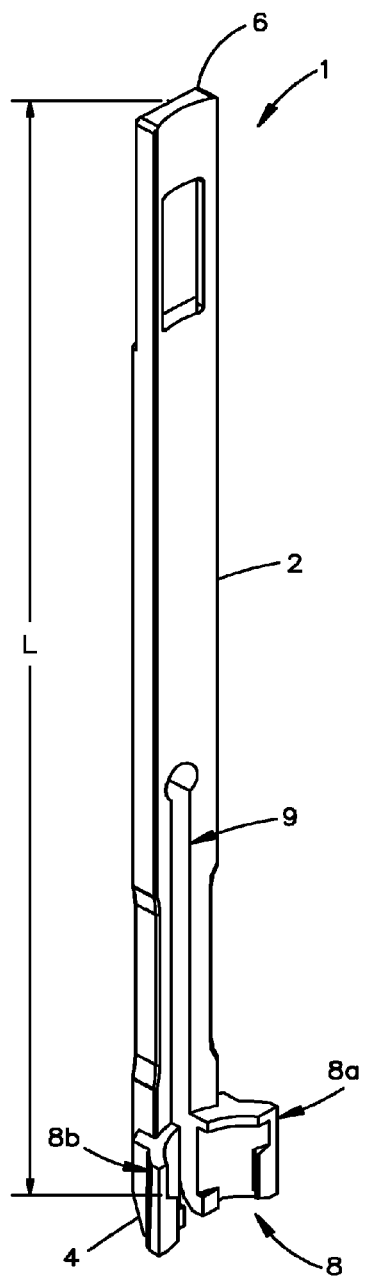
FIG. 1 is a perspective view of an exemplary embodiment of a lateral implant holder.

Certain exemplary embodiments of the invention will now be described with reference to the drawings. In general, such embodiments relate to a fixation system, by way of non-limiting example, a less invasive or minimally invasive fixation system for posterior spine fixation surgery using pedicle screws, preferably in the lumbar region of the spine. The fixation system including, for example, the implants and instruments are not limited to spine fixation, or posterior spine fixation and may have other uses and may come in different forms and structures. For example, the bone anchors are commonly shown and referred to as pedicle screws and may be polyaxial or mono-axial pedicle screw, as well as hooks (both mono-axial and polyaxial) or other fasteners, clamps or implants.

An embodiment of a fixation system in accordance with the present invention is directed to a minimally invasive system for posterior spinal fixation using pedicle screws, preferably in the lumber region of the spine, for example, for thoracolumbar pedicle fixation. The system may include a number of surgical instruments and/or devices to be used directly or indirectly with the bone anchors, for example, pedicle screws. Moreover, the system may allow the placement of multi-level screw/rod fixation constructs using fluoroscopy guidance with minimal trauma to the muscle, skin and other soft tissue. The system may also provide the capability for multi-level screw placement guidance, compression and distraction across the fixation construct, and rod persuasion.

While the present system will be described in the context of a spinal fixation procedure, those skilled in the art will appreciate that the system as well as the components thereof may be used for fixation in other parts of the body such as, for example, long bones or bones in the hand, face, feet, etc.

The various components of the fixation system may be made of, by way of non-limiting example, stainless steel, aluminum, titanium, titanium alloy, plastic, polymer, ceramic or any other biocompatible material. Non-glare or matte black coatings may be used to minimize refection and glare from lighting systems during the surgical procedure. The components may be radio opaque or may be radio transparent with radio opaque markers to assist a surgeon in visualizing the system when using x-rays or a fluoroscope.

Referring generally to the FIGS., the fixation system of the present invention may include one or more surgical instruments for performing a less invasive or minimally invasive surgical fixation procedure. For example, the fixation system may include a holding assembly, as generally shown in FIGS. 1-13. As will be described in greater detail below, the holding assembly preferably includes a lateral implant holder preferably operably associated with a sleeve. The holding assembly being sized and configured to securely engage the bone anchor head SH formed on the bone anchor, for example, pedicle screw PS being inserted. The holding assembly preferably is also sized and configured to be partially inserted into the body through an incision made in the patient's skin. The holding assembly is sized and configured so that it extends from the surgical site to be repaired, exterior of the patient so that a surgeon can preferably hold the proximal end of the holding assembly from outside the patient to manipulate the distal end thereof.

The fixation system of the present invention may optionally also include a holding sleeve, which when used in conjunction with the holding assembly facilitates insertion and fastening of the pedicle screw into the patient's bone.

The fixation system of the present invention may optionally also include a rod holder to facilitate insertion of a spinal rod R into the site of the procedure. Preferably, when used in combination with the holding assembly, the holding assembly includes or provides a passageway, portal or access for the rod holder to be inserted, and for providing visualization of the rod as it is being inserted and positioned.

The fixation system of the present invention may also include a compressor/distractor assembly for moving two or more inserted pedicle screws PS, and hence to move two or more vertebras that are attached thereto, with respect to one another.

It should be understood that those of ordinary skill in the art will recognize many modifications and substitutions which may be made to various elements of the fixation system. For example, one of ordinary skill in the art will understand that the different surgical instruments being described can be used and/or sold independently of one another or different components can be packaged as a set. In addition, one of ordinary skill in the art will understand that various different types of pedicle screws may be used in conjunction with the present invention, such as, polyaxial pedicle screws, mono-axial pedicle screws, pedicle hooks, etc., and in no way is the invention to be limited by the pedicle screw being described herein. One preferred type of pedicle screw is the Cannulated Pangea™ pedicle screw by Synthes (U.S.A.).

As shown in FIG. 1, the lateral implant holder 1 may include an elongated member 2 having a distal end 4, a proximal end 6, and an engagement portion 8 preferably located at the distal end 4. The lateral implant holder 1 may also include a flange 14 (shown in FIGS. 3 and 4) sized and configured to contact and/or engage a thumb knob assembly 12, as will be described in greater detail below. The lateral implant holder 1 may have a length L of, for example, between 50 mm and about 150 mm, more preferably between about 80 mm and about 120 mm.

The engagement portion 8 of the lateral implant holder 1 is preferably sized and configured to engage a pedicle screw PS. More preferably, the engagement portion 8 of the lateral implant holder 1 is sized and configured to engage a screw head SH formed on the pedicle screw PS. The lateral implant holder 1 is preferably sized and configured to engage the side of the screw head SH of the pedicle screw PS so that the rod-receiving channel formed in the pedicle screw PS is free of any obstructions. The lateral implant holder 1 is preferably sized and configured so that in use the engagement portion 8 engages the pedicle screw PS and is positioned below the patient's skin to hold and manipulate the pedicle screw PS below the skin and the lateral implant holder 1 extends up through the skin incision SI (as best shown in FIG. 26) to allow for locational visibility, screw head orientation, and screw manipulation by the surgeon. The lateral implant holder 1 may also provide a mounting point for other surgical instruments. In use, after a small skin incision SI is made, the muscle of the patient's body is preferably moved aside (i.e., not cut) by: using the surgeon's finger and moving it to split, but not cut, the muscle fibers, by sequential dilatation, or by other instruments and/or methods known in the art.

As shown in FIG. 1, the engagement portion 8 of the lateral implant holder 1 may be curved to closely match and engage the curved outer surface of the screw head SH. Moreover as shown, the engagement portion 8 may include first and second jaw members 8a, 8b which are preferably sized and configured to engage a portion of the pedicle screw PS, preferably a portion of the screw head SH. The first and second jaw members 8a, 8b may be separated by a longitudinal slot 9 which preferably extends from the distal end 4 of the lateral implant holder 1 towards the proximal end 6 of the lateral implant holder 1. Such an arrangement enables the first and second jaw members 8a, 8b to flex or move relative to one another so that the screw head SH, which is being inserted into the engagement portion 8, may be received within the first and second jaw members 8a, 8b. Once the screw head SH is received by the engagement portion 8, the first and second jaw members 8a, 8b are preferably biased so that the first and second jaw members 8a, 8b flex toward each other and towards the received screw head SH so that the first and second jaw members 8a, 8b snap onto the screw head SH and retain the screw head SH therebetween. The first and second jaw members 81, 8b may be configured so that when they flex back toward each other to retain the screw head SH, they exert a force on the screw head SH to assist in retaining the screw head SH, or alternatively, the jaw members 8a, 8b may be configured so that when they flex back toward each other, they do not exert a force on the screw head SH but still retain the screw head SH as a result of flanges, recesses or other structures and/or means.

Moreover, the first and second jaw members 8a, 8b may each include at least one protrusion (not shown) which are sized and configured to engage a groove (not shown), or other attachment feature, formed in the screw head SH of the pedicle screw PS. This configuration provides additional protection for preventing the displacement of the screw head SH with respect to the engagement portion 8, and thus facilitates maintaining the pedicle screw PS in place.

In one embodiment, the proximal end 6 of the lateral implant holder 1 (i.e., the portion which remains outside the skin incision SI) may be laterally offset (not shown), for example, the shaft portion of the lateral implant holder 1 may be curved, from the centerline of the screw to offset the proximal end 6 of the lateral implant holder 1 away from the visual surgical field. This offset prevents obstruction of the visual field for the surgeon and may increase the physical access space during the surgical procedure.

Figure 2:
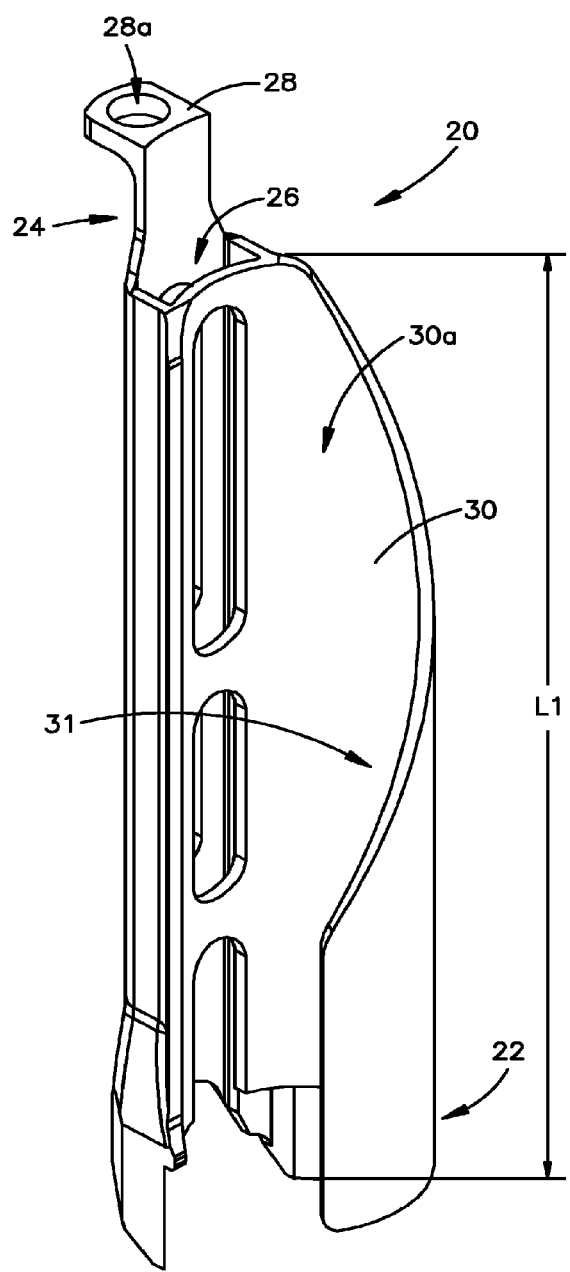
FIG. 2 is a perspective view of an exemplary embodiment of a sleeve.

As best shown in FIG. 2, in order to further prevent the lateral implant holder 1 from separating from the screw head SH, the holding assembly 3 may include a sleeve 20, the sleeve 20 being sized and configured to fit over or engage the lateral implant holder 1 and to ensure that the first and second jaw members 8a, 8b do not flex away from one another. The sleeve 20 may be integral with or attached to the lateral implant holder 1 and may be provided in different lengths L1, for example, the sleeve may have a length L1 of between about 30 mm and about 140 mm, more preferably between about 40 mm and about 120 mm and, most preferably, between about 60 mm and 90 mm and a diameter D, for example, of between about 9 mm and about 15 mm, more preferably between about 10 mm and about 14 mm and, most preferably, between 12 mm and about 13 mm. In some embodiments, the sleeve 20 may be added, removed and/or replaced during the surgical procedure at the discretion of the surgeon. The sleeve 20 is preferably sized and configured to bias the first and second jaw members 8a, 8b at the distal end 4 of the lateral implant holder 1 towards one another and thus toward the screw head SH to ensure that the lateral implant holder 1 does not release the pedicle screw PS. Alternatively, the sleeve 20 may be configured so that it does not exert a force on the first and second jaw members 8a, 8b but rather, slides over the first and second jaw members 8a, 8b to prevent the first and second jaw members 8a. 8b from expanding (i.e., to prevent the first and second jaw members 8a, 8b from separating a sufficient distance which would permit the pedicle screw PS to be displaced from the lateral implant holder 1). As shown, the sleeve 20 may be an elongated member having a distal end 22 and a proximal end 24. The sleeve 20 being moveable with respect to the lateral implant holder 1 between a first position shown in FIG. 3 and a second position shown in FIG. 4. In the first position, the distal end 22 of the sleeve 20 is positioned away from the engagement portion 8 of the lateral implant holder 1. In the second position, the distal end 22 of the sleeve 20 may be positioned over the engagement portion 8 of the lateral implant holder 1, thereby further retaining, engaging or biasing the lateral implant holder 1 to the pedicle screw PS depending upon the design desired.

As best shown in FIG. 2, the sleeve 20 may also include a passageway (i.e., an opening) 26 for receiving the lateral implant holder 1 therethrough. The sleeve 20 may further include a flange 28 having an aperture 28a. The flange 28 being sized and configured to contact the thumb knob 12, as will be described in greater detail below. It should be further noted that the lateral implant holder 1 may be displaceable with respect the sleeve 20 by any means known in the art.

In one preferred embodiment (as best shown in FIGS. 3 and 4), movement of the sleeve 20 with respect to the lateral implant holder 1 may be accomplished by a thumb knob assembly 12. The thumb knob 12 is preferably sized and configured to facilitate displacement of the sleeve 20 with respect to the lateral implant holder 1, preferably along the length of the lateral implant holder 1, as will be readily understood by one of ordinary skill in the art.

As shown in FIG. 3, the thumb knob 12 may be positioned, for example, at the proximal end 6 of the lateral implant holder 1. The thumb knob 12 is preferably configured so that it is rotatable relative to the lateral implant holder 1. For example, the lateral implant holder 1 may include a flange 14 having an aperture 14a for receiving a threaded rod 19. As shown, the thumb knob 12 may be received on he threaded rod 19 and positioned between the flange 14 of the lateral implant holder 1 and the flange 28 of the sleeve 20. Preferably, the threaded rod 19 is sized and configured to be fixed with respect to one of the flanges 14, 28, preferably with respect to flange 28. Moreover, preferably the aperture 14a formed in the flange 14 of the lateral implant holder 1, the aperture 28a formed in the flange 28 of the sleeve 20, and a threaded bore (not shown) formed in the thumb knob 12 are sized and configured to receive the threaded rod 19 so that rotation of the thumb knob 12 results in movement of the sleeve 20 with respect to the lateral implant holder 1. As shown, preferably the aperture 14a formed on the flange 14 of the lateral implant holder 1, the aperture 28a formed on the flange 28 of the sleeve 20, and the threaded bore formed in the thumb knob 12 are coaxially arranged along an axis 17.

Figure 7:
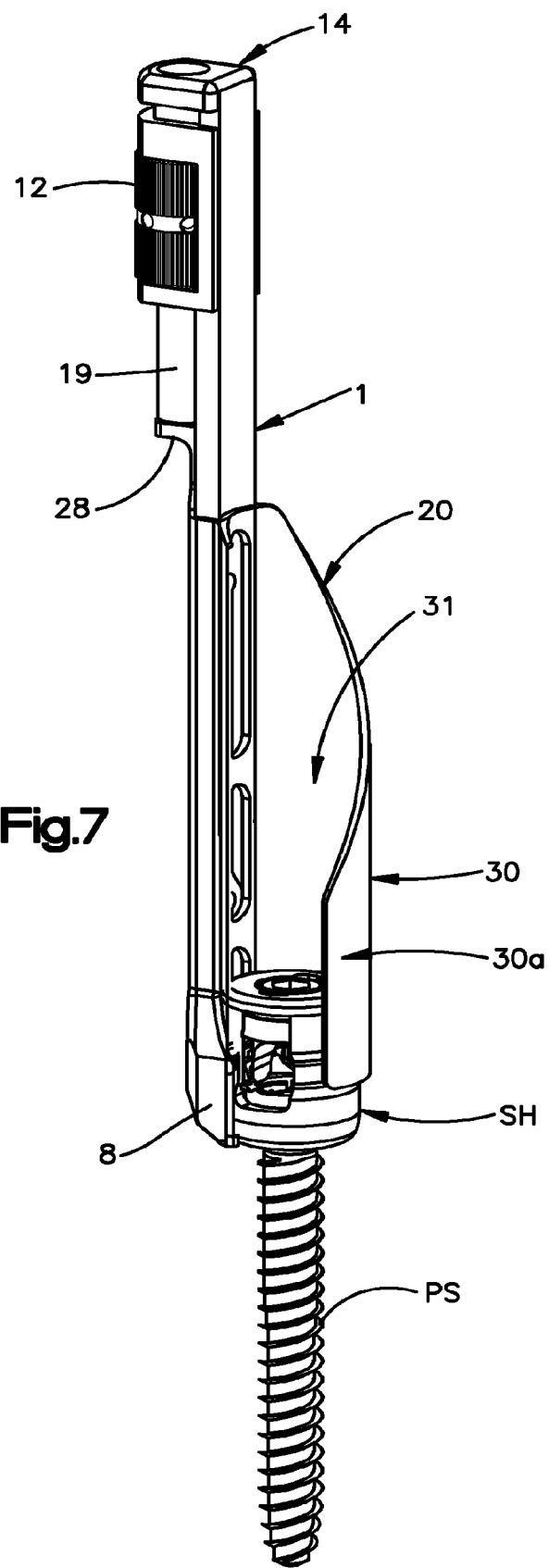
FIG. 7 is a perspective view of the construct of FIG. 4 engaging a bone anchor, for example, a bone screw.
Figure 7A:
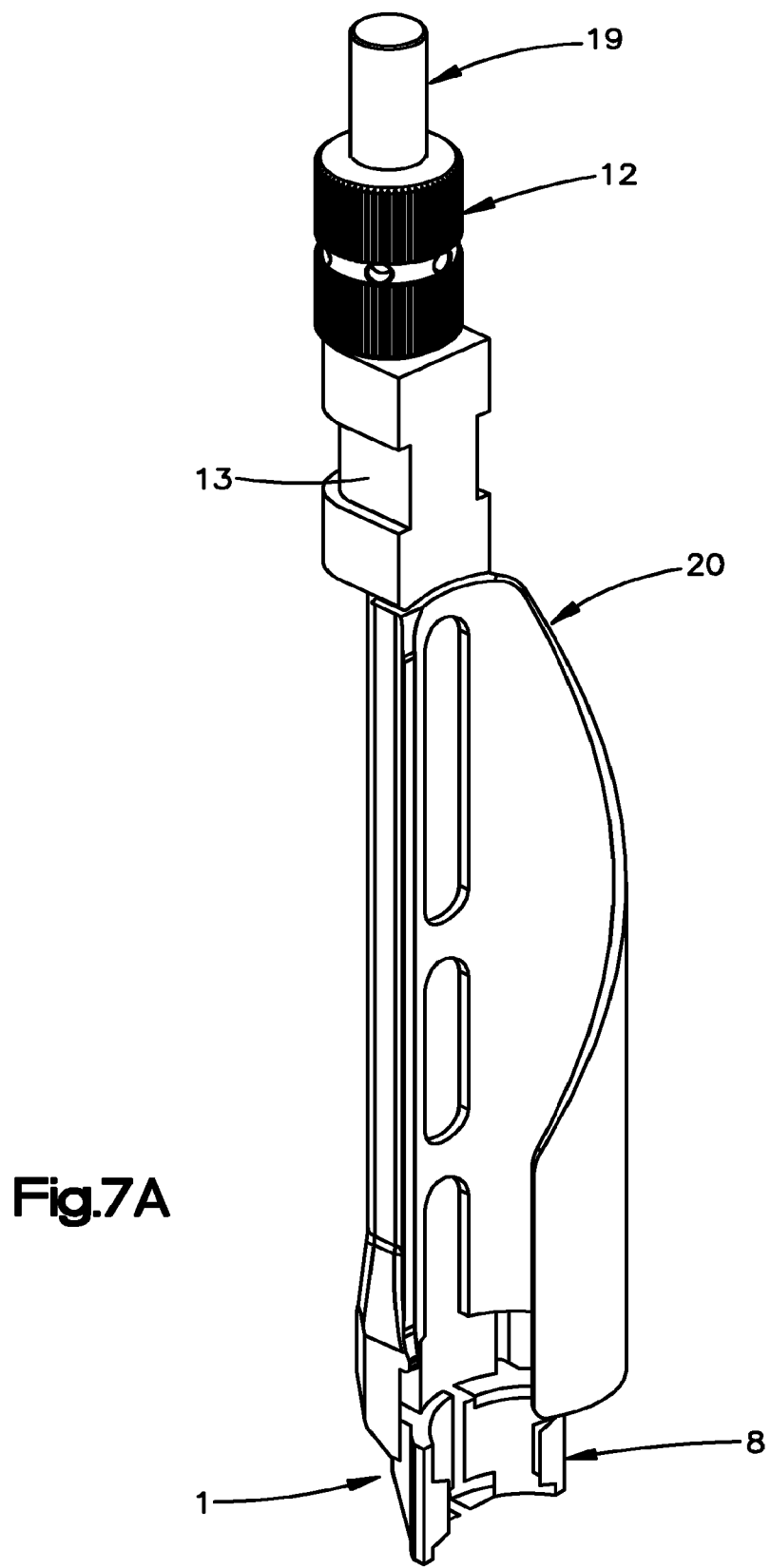
FIG. 7a is a side view of an alternate embodiment of the lateral implant holder with the sleeve attached thereto.

Alternatively, as shown in FIG. 7a, the thumb knob 12 may contain a cavity (not shown) for contacting and/or engaging the lateral implant holder 1. The threaded rod 19 being sized and configured to contact and/or engage a portion of the sleeve 20, preferably the flange 28, such that rotation of the thumb knob 12 causes the sleeve 20 to move with respect to the lateral implant holder 1. Moreover preferably the thumb knob 12 includes a groove 13 formed therein for engaging the handle 104 of the holding sleeve 100, as will be described in greater detail below.

Alternatively, the flange 14 of the lateral implant holder 1 and the flange 28 of the sleeve 20 may be located adjacent to one another and the thumb knob 12 may be located on either side, for example, the thumb knob 12 may be located proximally of the flanges 14, 28 (not shown).

Referring back to FIGS. 3 and 4, in use, one end 19a of the threaded rod 19 may be positioned against one of said flanges 14, 28, preferably flange 28 of the sleeve 20. Preferably, end 19a of the threaded rod 19 is fixedly connected to the flange 28 of the sleeve 20. The other end 19b of the threaded rod 19 may be positioned against the flange 14 of the lateral implant holder 1 or through an aperture 14a formed in the flange 14. Moreover, the aperture 14a may be threaded so as to threadably engage the threaded rod 19. The rod end 19b is preferably sized and configured so as to enable the threaded rod 19 to extend through the aperture 14a. In use, rotation of the thumb knob 12 causes the threaded rod 19 to rotate, which in turn, as will be readily appreciated by one of ordinary skill in the art, causes the sleeve 20 to move proximally or distally with respect to the lateral implant holder 1. This in turn causes the sleeve 20 and the lateral implant holder 1 to move between the first position, wherein the distal end 22 of the sleeve 20 is positioned away from the engagement portion 8 of the lateral implant holder 1, shown in FIG. 3, and the second position, wherein the distal end 22 of the sleeve 20 is positioned over the engagement portion 8 of the lateral implant holder 1 to further bias the lateral implant holder 1 to the pedicle screw PS, shown in FIG. 4.

The sleeve 20 may also include one or more tissue protection portions 30, which may be sized and configured to prevent the tissue surrounding the surgical workspace from entering the surgical workspace. Tissue entering the surgical workplace may hinder the insertion of other surgical instruments and/or devices as well as obstruct the surgeon's view of the surgical workplace. The tissue protection portion(s) 30 may be integrally formed with the sleeve 30 or, alternatively, may be formed as a separate component, attachable thereto. Moreover, the design of the tissue protection portion(s) 30 may be customized to provide enhanced tissue retraction which allows for general decompression, discectomy, interbody fusion, and/or lateral fusion procedure.

Figure 28:
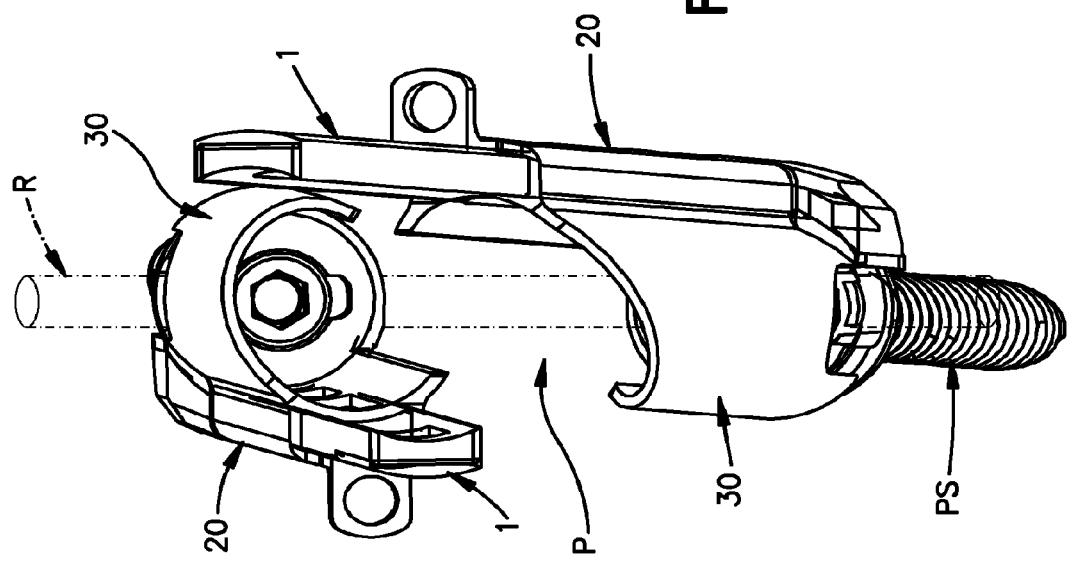
FIG. 28 is a top view of the assembly of FIG. 26.

The tissue protection portion 30 preferably is sized and configured to form a passageway for receiving additional surgical instruments and/or devices. That is, the sleeve 20 and tissue protection portions 30 are preferably sized and configured to form helices 30a that define a passageway or opening 31 between the lateral implant holder 1 and the tissue protection portion 30 so that adjacent sleeves 20 may be positioned in close proximity to one another without interfering (or having minimal interference) with each other. As shown, the tissue protection portions 30 may be configured so that they form a partial cylindrical tube, preferably having a side opening 29. More preferably, the tissue protection portion 30 has a distal end that is positioned proximate the pedicle screw PS and a proximal end that preferably extends out of the skin incision SI to the exterior of the patient. The distal end preferably extends around, for example, between about 250 degrees to about 300 degrees, more preferably about 270 degrees. The distal end of the tissue protection portion 30 has a height H, for example, of about 10% to about 90%, more preferably about 15% to about 40%, and most preferably about 25% to about 33% of the length L1 of the sleeve 20. The proximal part of the tissue protection portion 30, including the helices 30a are preferably cut away (i.e., removed) so that the proximal part of the helices 30a does not extend as far around as the distal end. That is, as shown in FIGS. 2-4, the first and second tissue protection portions have cut outs or removed sections, the cut outs may be in the form of a helical shape or spiral to form helices 30a. Preferably, the helices 30a transitions from the proximal end of the tissue protection portion 30 (which is preferably exterior to the patient when in use) to an intermediate point (which may be within the patient) via an inclined surface. Aligning (or intermeshing) of adjacent tissue protection portions 30 forms a passageway P for inserting and/or guiding instrumentation into the surgical site. For example, as best shown in FIG. 28, the tissue protection portions 30 may form a passageway P or elongated slot for guiding the rod R into the screw heads SH of the pedicle screw PS.

Figure 5:
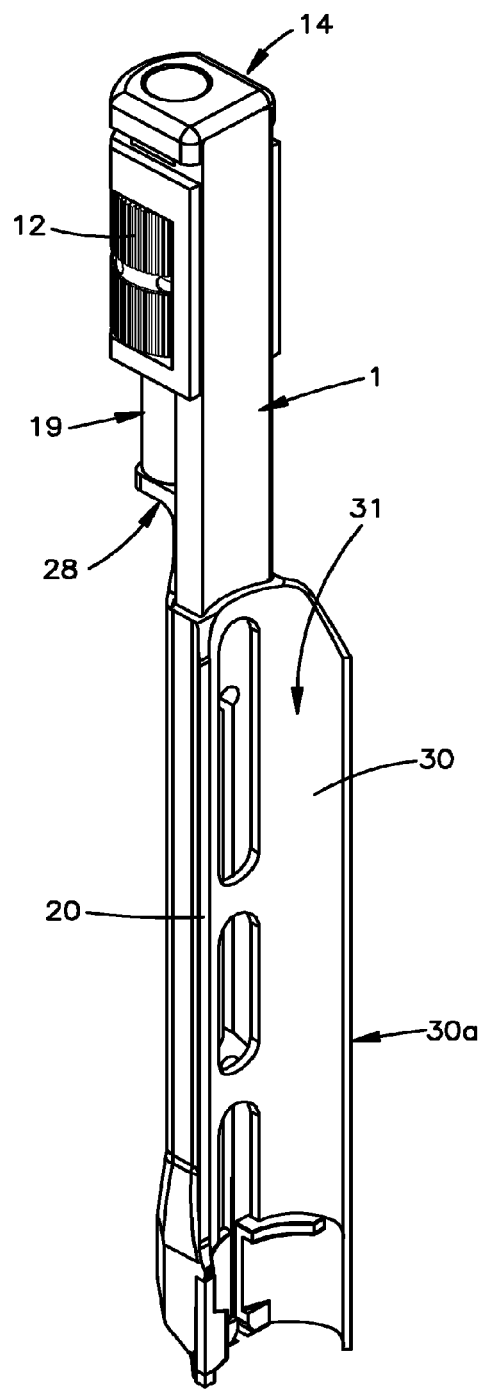
FIG. 5 is a perspective view the lateral implant holder of FIG. 1 with an alternative exemplary sleeve attached thereto.
Figure 6:
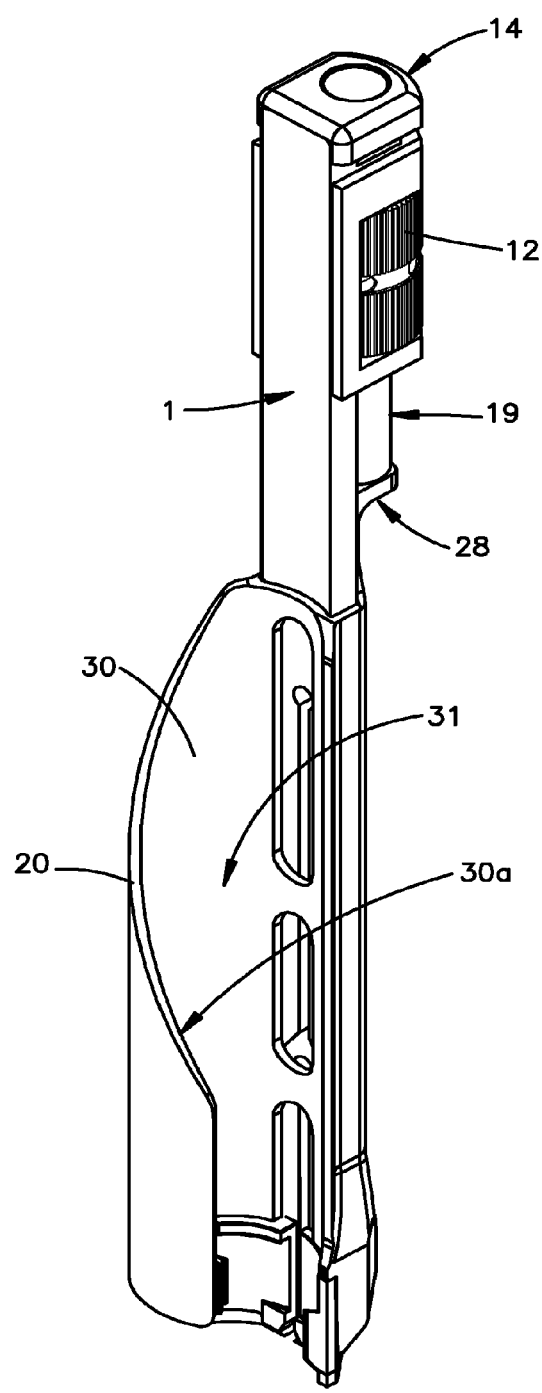
FIG. 6 is a perspective view of the lateral implant holder of FIG. 1 with another alternative exemplary sleeve attached thereto.
Figure 13:
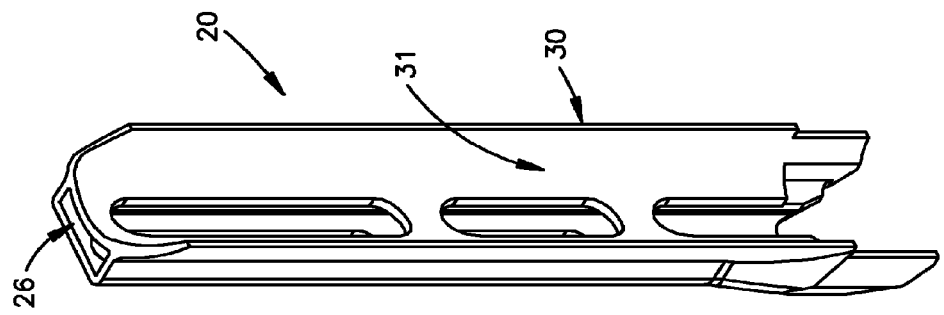
FIG. 13 is a perspective view of an embodiment of a sleeve.
Figure 12:
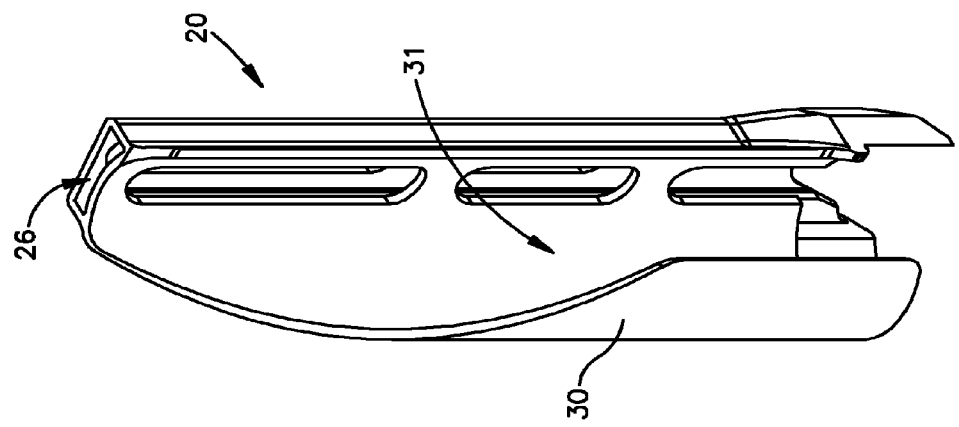
FIG. 12 is a perspective view of an embodiment of a sleeve.
Figure 11:
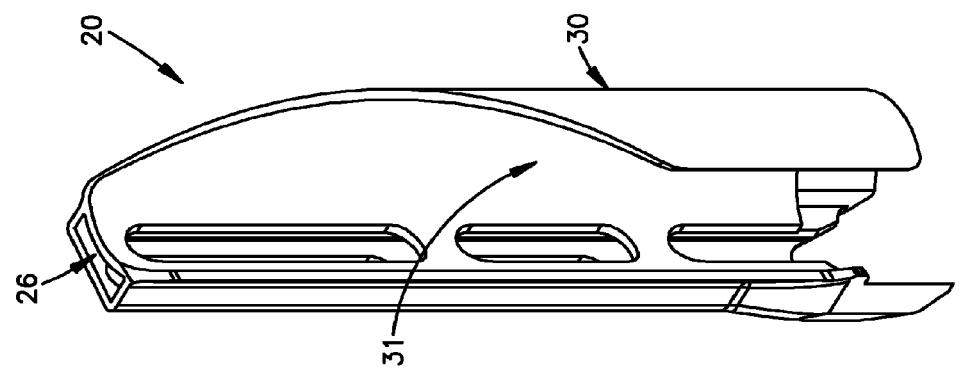
FIG. 11 is a perspective view of an embodiment of a sleeve.

In use, once the pedicle screws PS and the holding assembly 3 are in place, arranging the tissue protection portions 30 so that the helices 30a are intermeshed provides improved tissue protection, maximum visualization, and reduced trauma by reducing the overall size of the skin incision SI. Intermeshing of the helices 30a may be accomplished by ensuring that every other opening of the helices 30a, faces one another. That is, as best shown in FIGS. 4-6, 11-13 and 26-29, the tissue protection portion(s) 30 and helices 30a may have various geometries and configurations to provide varying levels of tissue protection based on surgeon preference and the fixation elements being implanted. The tissue protection portion(s) 30 may allow for enhanced visibility and access along the entire surgical workspace. For example, the tissue protection portion 30 may be in the form of a right-handed sleeve 20, as best shown in FIGS. 4 and 11, a center-style sleeve 20, as best shown in FIGS. 5 and 13, or a left-handed sleeve 20, as best shown in FIGS. 6 and 12. It may be preferable to provide a different color for each of the left, center, and right handed sleeves 20 to facilitate correct selection and reduce the risk of an incorrect sleeve 20 being utilized. As shown in FIGS. 26-29, a right-handed sleeve and a left-handed sleeve may be positioned such that the tissue protection portions face one another (i.e., intermesh) so that a passageway P or elongated slot is created thus providing a larger field of view of the surgery site within the body. The center-style sleeve may also be positioned between the right and left-handed sleeves to create an even larger passageway P or elongated slot. In this way, a surgeon can create a relatively larger working space within the patient's body as compared to the size of the skin incision SI, as best shown in FIGS. 26-29, thus minimizing the amount of associated trauma.

It is envisioned that the various styled sleeves 20 can be used in any number of configurations. For example, for a one-level procedure, it may be preferable to use a left handed sleeve and a right-handed sleeve whereas for a two or more-level procedure, it may be preferable to use a right handed sleeve, a left handed sleeve and one or more center-style sleeves between the left and right-handed sleeves. Alternatively, for a single level construct, two right handed or two left handed sleeves may be used. Selection of two right handed or two left handed sleeves allows for improved intermeshing of the helices and provides excellent access to the patient's bone. Moreover, the selection of two right handed sleeves may be preferred for a procedure on the left side of the patient while the selection of two left handed sleeves may be preferred for a procedure on the right side of the patient. Those skilled in the art will appreciate that the sleeve 20 and tissue protection portion 30 may take on other shapes.

It should be further noted that in some embodiments, the sleeve 20 and/or tissue protection portion(s) 30 may be eliminated. For example, in the embodiment of the lateral implant holder 50 shown in FIGS. 8 and 9, the lateral implant holder 50 may include a locking feature, for example, an internal locking feature, which securely engages the screw head SH of the pedicle screw PS, thus making the sleeve 20 optional and/or unnecessary. That is, as shown, the engagement portion 52 of the lateral implant holder 50 may have first and second jaw members 52a, 52b which securely engage the screw head SH. FIGS. 8 and 9 illustrate an embodiment of the lateral implant holder 50 designed such that the offset from the center axis X-X of the pedicle screw PS to the body of the lateral implant holder 50 is minimized. The distal end 54 of the lateral implant holder 50 may also be chamfered to remain as close to the screw PS as possible. Such a configuration may minimize obstruction to screw head mobility when the screw PS is implanted and may minimize the skin incision SI required for screw placement. In an embodiment without tissue protection portions, lateral implant holders 50 may be alternately oriented (e.g., medial-lateral-medial) to provide a slotted channel SC for rod placement. In another configuration, the lateral implant holders 50 may be placed all medially or all laterally to provide a planar surface to guide surgical instruments and/or devices (e.g., a rod R) into the screw heads SH. Those skilled in the art will appreciate that any lateral implant holder with internal locking may be similarly configured.

Figure 10:
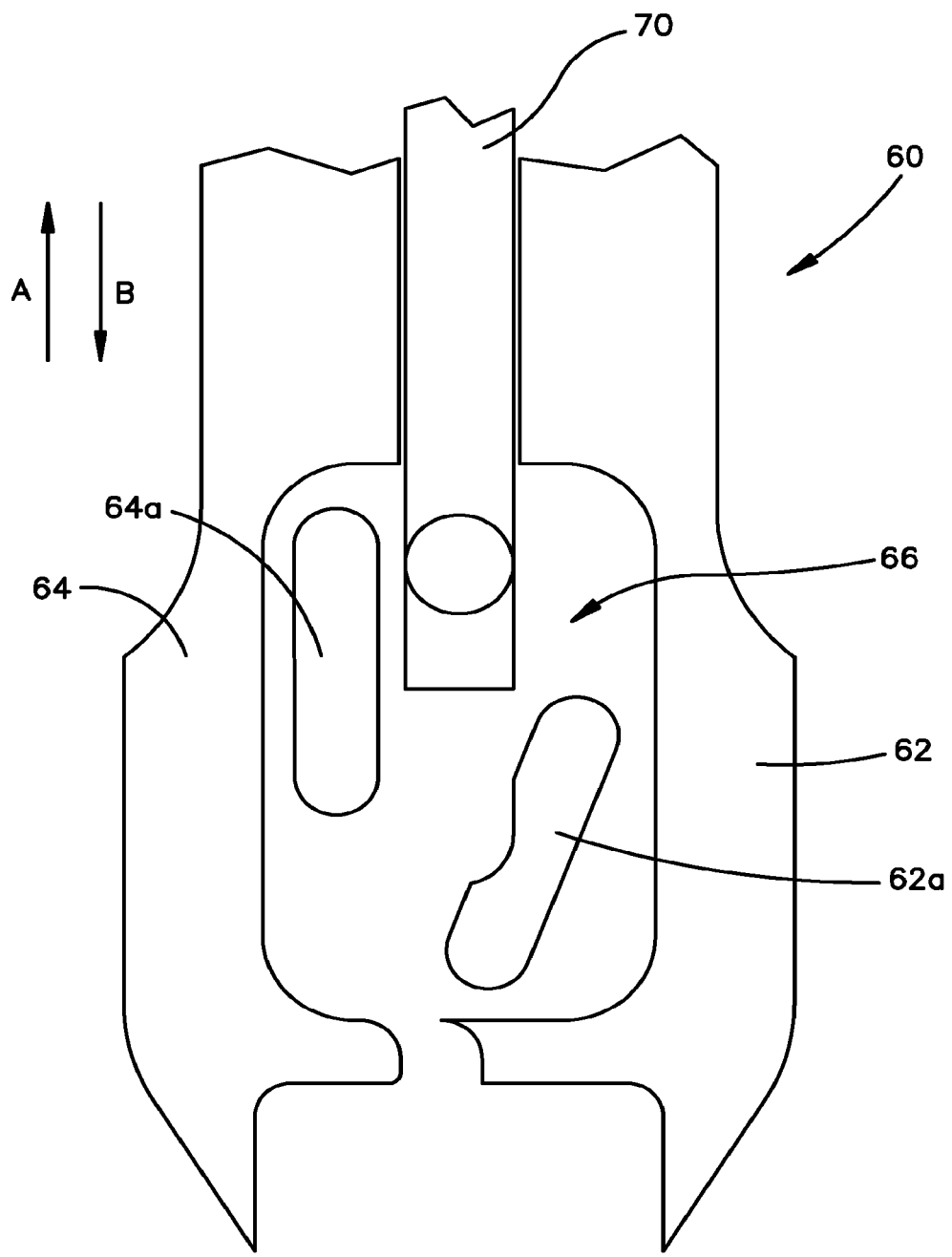
FIG. 10 is a back view of an end of an alternative lateral implant holder with a locking mechanism.

An exemplary example of an internal locking mechanism is shown in FIG. 10, the lateral implant holder 60 may include first and second arms 62, 64 and a wedge plate 66 for attaching the first and second arms 62, 64. Each of the first and second arms 62, 64 preferably includes a pin 62a, 64a. Preferably, pin 62a is a wedge pin 62a and pin 64a is a static pin 64a, although pin 62a may be the static pin and pin 64a may be the wedge pin. The pins 62a, 64a are sized and configured to be positioned in a respective slot (not illustrated) formed in the wedge plate 66 such that as the wedge plate 66 moves, the first and second arms 62, 64 move towards and/or away from each other. The lateral implant holder 60 preferably also includes an actuation rod 70, which may be engaged with the wedge plate 66 to facilitate moving the wedge plate 66 distally and/or proximally as the actuation rod 70 is moved along the length of the lateral implant holder 60. For example, when the actuation rod 70 is pulled in direction A toward the proximal end (not shown) of the lateral implant holder 60, the wedge plate 66 is moved in direction A, driving the wedge pin 62a closer to the static pin 64a. In this way, the lateral implant holder 60 may be securely attached to the pedicle screw PS. The lateral implant holder 60 may be released from the pedicle screw PS by moving the actuation rod 70 distally in direction B, and hence the wedge plate 66, toward the distal end (not shown) of the lateral implant holder 60. This, in turn, causes the wedge pin 62a and the static pin 64a to move away from one another, thereby allowing the first and second arms 62, 64 to spread and release the screw head SH of the pedicle screw PS.

Figure 14:
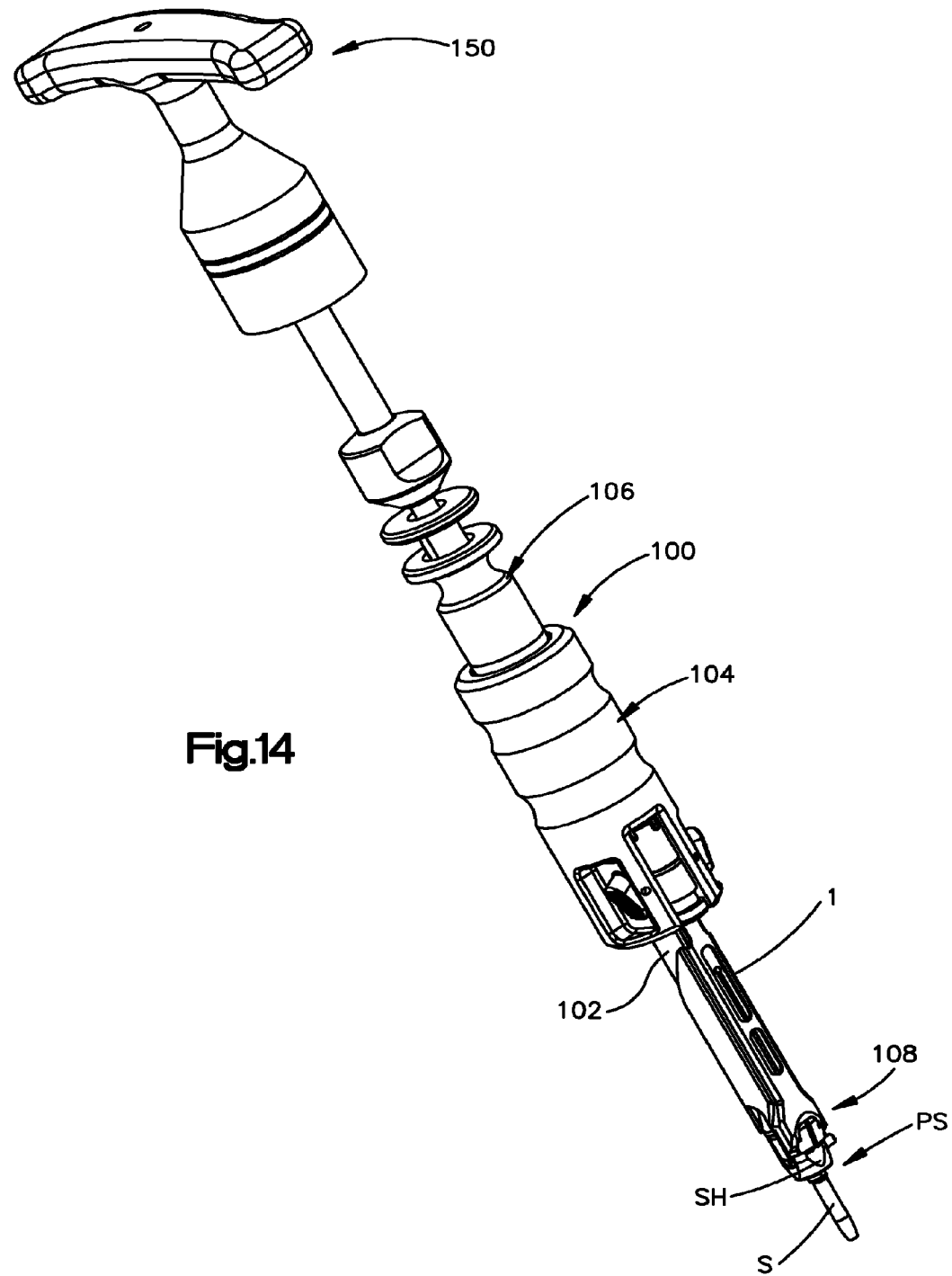
FIG. 14 is a perspective view of an embodiment of a holding sleeve, driving mechanism and bone anchor construct.
Figure 15:
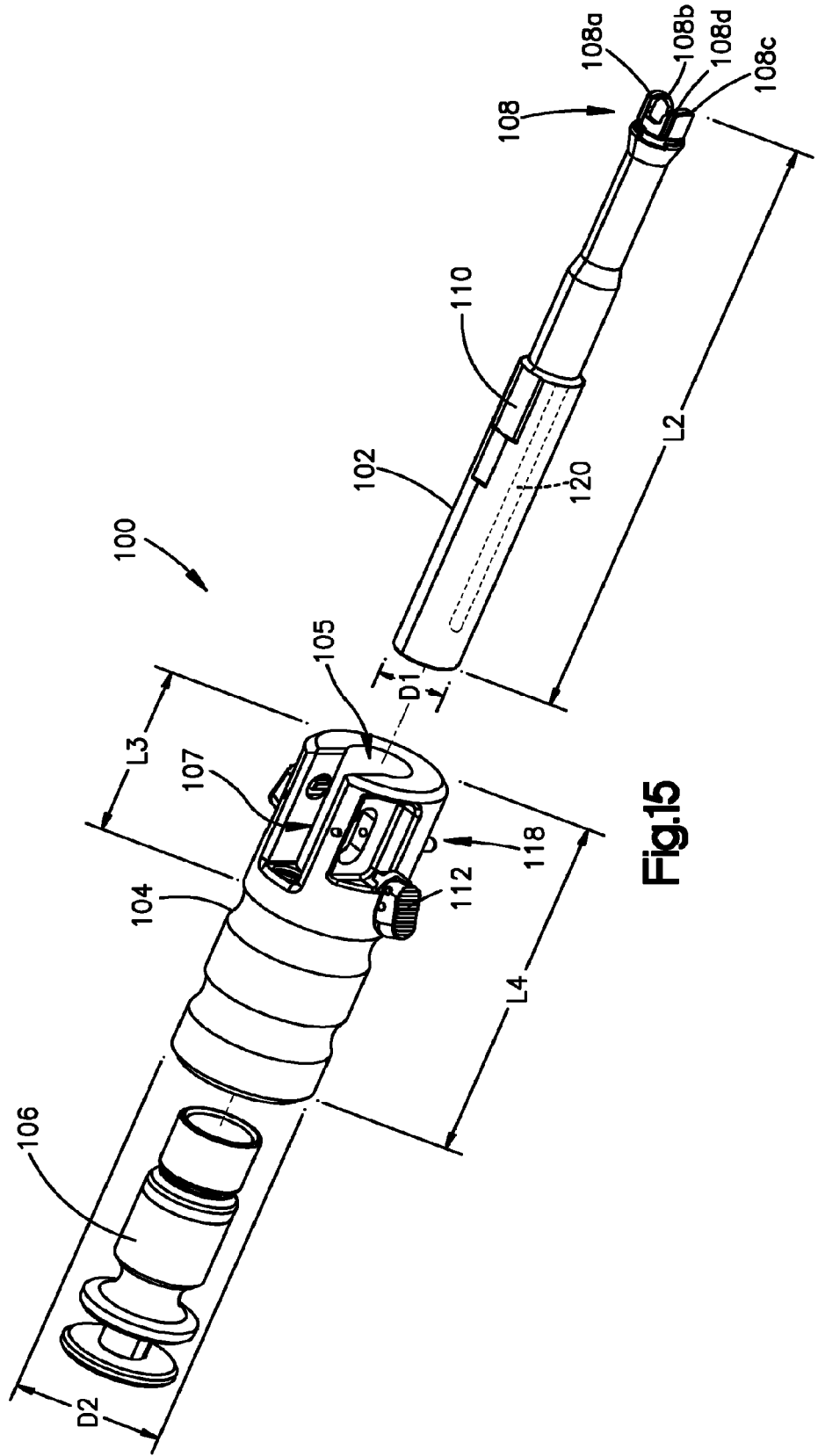
FIG. 15 is an exploded perspective view of an embodiment of a holding sleeve.
Figure 16:
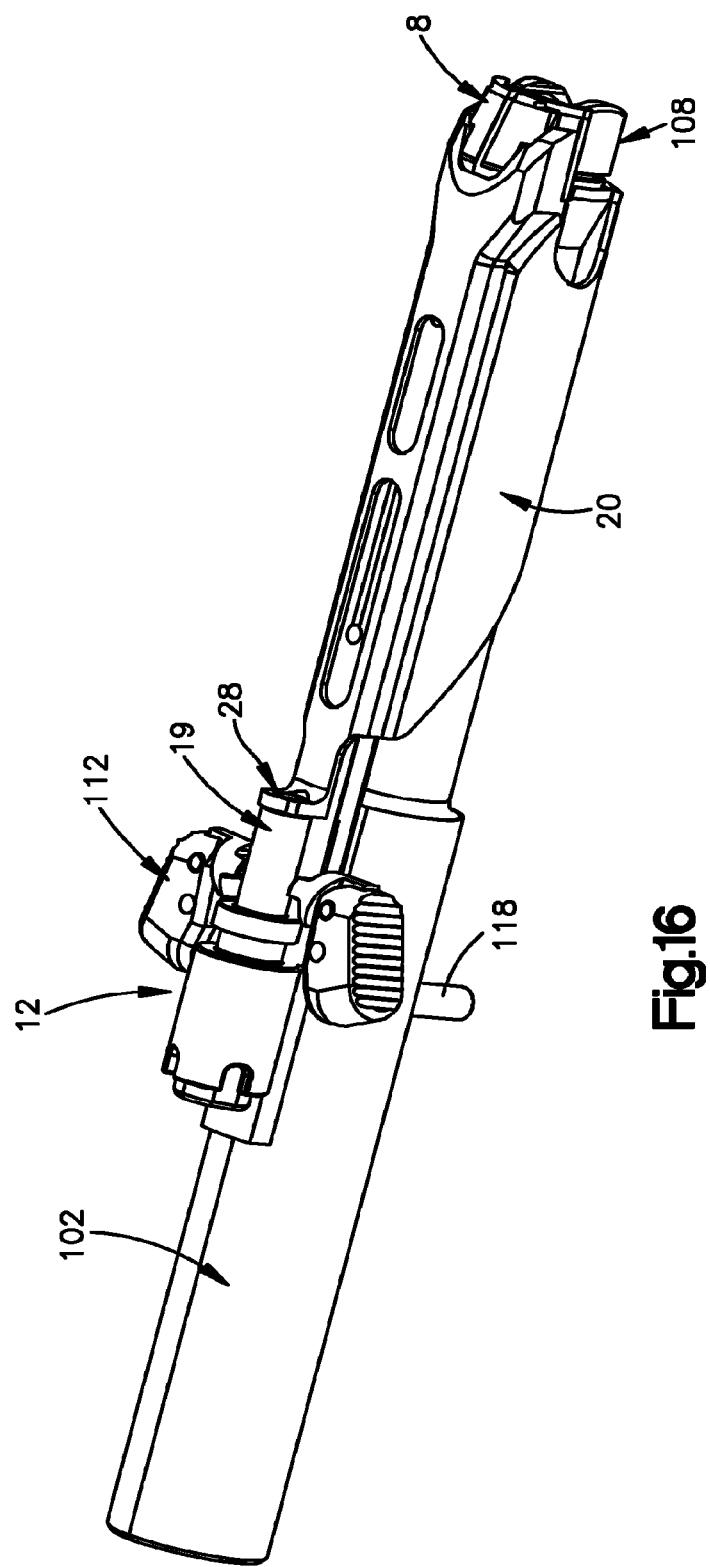
FIG. 16 is a perspective view of a portion of an embodiment of a holding sleeve, sleeve and lateral implant holder assembly.

As shown in FIGS. 14 and 15, the fixation system may also include a holding sleeve 100. As will be described, the holding sleeve 100 is used to insert the pedicle screw PS into a vertebra. Use of the holding sleeve 100 will be described in conjunction with the holding assembly 3, although it is envisioned that the holding sleeve 100 is independent of the holding assembly 3 and, as such, the holding sleeve 100 may be used with other known surgical instruments including other holding assemblies.

As shown, the holding sleeve 100 may be configured to operate in conjunction with the holding assembly 3 (i.e., the lateral implant holder 1 and sleeve 20), the pedicle screw PS and/or the driving mechanism 150. The holding sleeve 100 preferably prevents rotation and/or toggling of the screw head SH relative to the screw portion S of the pedicle screw PS. More specifically, using the holding sleeve 100, a surgeon may position the pedicle screw PS, the holding assembly 3 and/or the driving mechanism 150 into the body as a single unit, for example, as illustrated in FIG. 14. During the procedure, the surgeon may grasp the holding sleeve 100 while manipulating the driving mechanism 150.

The holding sleeve 100 engages the screw head SH of the pedicle screw PS and the driving mechanism 150 engages the screw portion S of the pedicle screw PS so that movement of the driving mechanism 150 with respect to the holding sleeve 100 causes the screw portion S of the pedicle screw PS to be rotated with respect to the screw head SH and thus causes the pedicle screw PS to be driven into the tissue (not shown). For example, the surgeon may rotate the driving mechanism 150 to insert the pedicle screw PS into a vertebra.

As shown in FIGS. 14 and 15, the holding sleeve 100 may include an elongated member 102, a handle 104, and an interconnecting member 106. The elongated member 102, the handle 104 and the interconnecting member 106 all preferably include a passageway (i.e., a through bore) 110 extending therethrough for receiving other surgical instruments such as, but not limited to, the driving mechanism 150 (e. g. screw driver, such as but not limited to a Cannulated StarDrive screwdriver by Synthes U.S.A.). The elongated member 102 may have a length L2, for example, of between about 120 mm and 220 mm and a diameter D1, for example, of between about 9 mm and about 15 mm, more preferably between 10 mm and about 14 mm and, most preferably, between about 12 mm and about 13 mm.

The elongated member 102 is preferably sized and configured to be received in the passageway 31 created by the tissue protection portion 30 of the sleeve 20 and to fix the orientation of the screw head SH relative to the holding assembly 3. As shown, the elongated member 102 may be circular or any other shape known in the art.

The distal end 108 of the elongated member 102 may have a plurality of moveable arms 108a, 108b, 108c, 108d which may be positioned into the screw head SH to prevent rotation of the screw head SH relative to the holding assembly 3 (i.e., the lateral implant holder 1 and sleeve 20). The moveable arms 108a, 108b, 108c, 108d may also include slots (not shown) therebetween so that the moveable arms 108a, 108b, 108c, 108d may flex upon insertion into the screw head SH. In this way, the arms 108a, 108b, 108c, 108d may exert a force onto the screw head SH, thereby preventing the screw head SH from moving relative to the holding assembly 3. In other embodiments, the elongated member 102 may have one or more protrusions (not shown) which may engage a U-shaped channel formed on the screw head SH so as to prevent movement of the screw head SH relative to the holding assembly 3.

Referring to FIG. 15, the handle 104 of the holding sleeve 100 preferably includes a first opening 105 (e.g., a slot or cavity), the opening 105 being sized and configured to receive the proximal end of the elongated member 102 therein. The handle 104 also preferably includes a second opening 107 (e.g., an elongated slot or cavity) for receiving the proximal end 6 of the lateral implant holder 1 such that the lateral implant holder 1 may be axially received within the opening 107. Preferably, the opening 107 is sized and configured to prevent the holding sleeve 100 from rotating with respect to the holding assembly 3. As such, the handle 104 of the holding sleeve 100 is preferably sized and configured to engage both the lateral implant holder 1 of the holding assembly 3 and the elongated member 102 while simultaneously being sized and configured to be received within the passageway 31 formed by the tissue protection portions 30 of the sleeve 20. The handle 104 may have a length L4, for example, of between about 80 mm and about 140 mm, more preferably of between about 90 mm and about 130 mm and, most preferably, between about 100 mm and about 120 mm and a diameter D2, for example, of between about 20 mm and about 50 mm, more preferably between about 25 mm and about 45 mm and, most preferably, between about 30 mm and about 40 mm. The second opening 107 may have a length L3, for example, of between about 10 mm and about 50 mm, more preferably between about 20 mm ad about 40 mm and, most preferably, between about 25 mm and about 35 mm.

The handle 104 may also include at least one push button 112 which preferably contacts and/or engages the proximal end 6 of the lateral implant holder 1. The push buttons 112 preferably incorporate at least one protrusion (not shown) formed thereon for engaging the annular groove 13 formed in the thumb knob 12 of the holding assembly 3 (as shown in FIG. 7a). Thus, in use, to insert the holding assembly 3 into the handle 104, the surgeon depresses the push buttons 112. Once the holding assembly 3 is properly positioned with respect to the handle 104, the push buttons 112 are released so that the protrusions formed on the push buttons 112 securely engage the annular groove 13 formed on thumb knob 12, thus securely engaging the lateral implant holder 1 and hence the holding assembly 3 to the holding sleeve 100. Alternatively, the push buttons 112 and protrusions formed thereon may be sized and configured to be flexible so that the proximal end 6 of the lateral implant holder 1 may be snapped into engagement with the handle 104. To release the holding sleeve 100 from the holding assembly 3, the surgeon presses push buttons 12, which causes the protrusions to disengage from the annular groove 13.

The handle 104 may also include a pin 118 which may be received in and axially moveable within a slot 120 formed in the elongated member 102. Such a construction allows the elongated member 102 to move axially but not rotationally relative to the handle 104. While shown as being cylindrical in shape, the handle 104 may be any shape known in the art and may also include a grip enhancing portion to increase a surgeon's grip on the holding sleeve 100.

Figure 17:
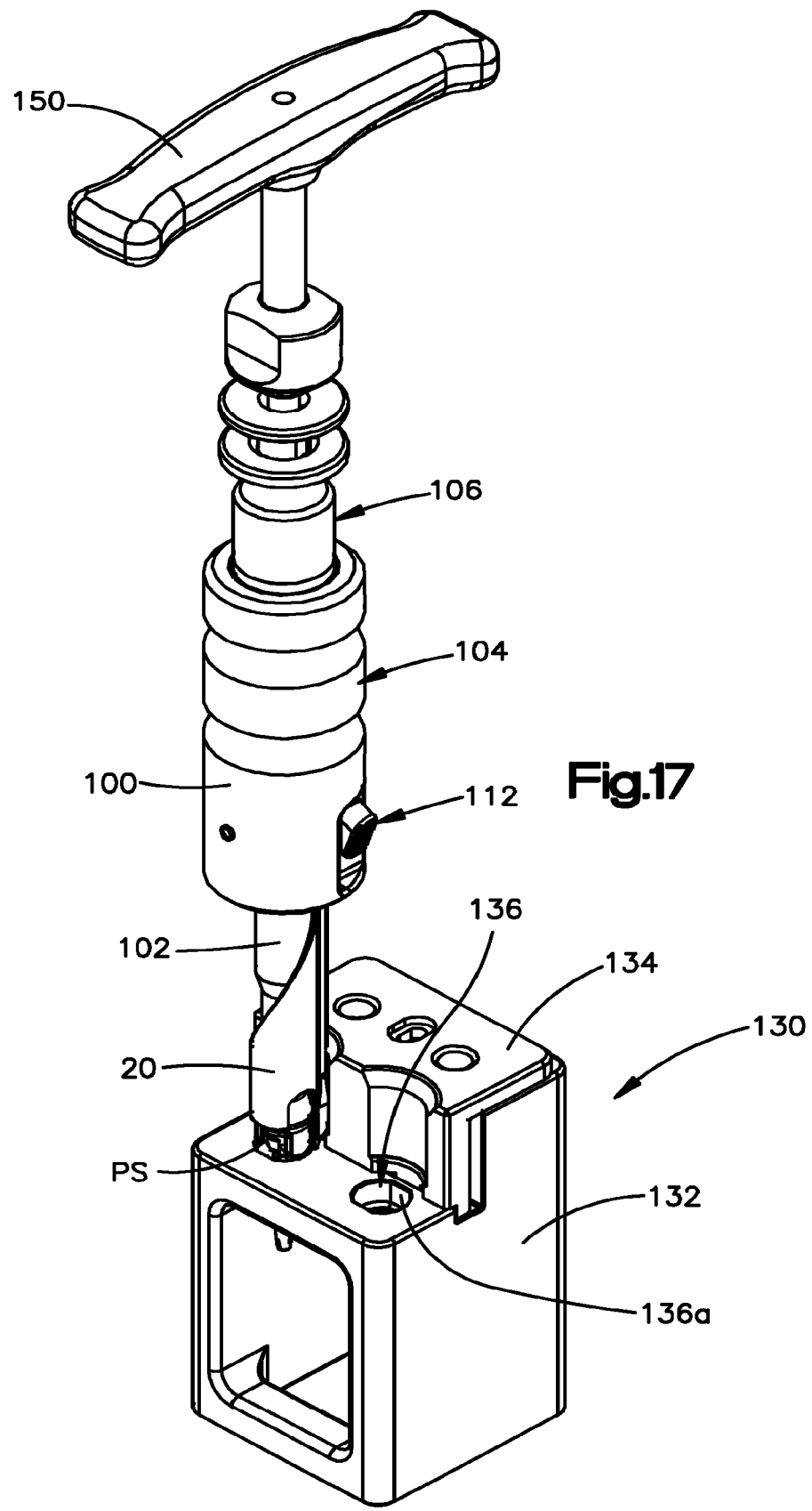
FIG. 17 is a perspective view of a loading station and the embodiment of the device of FIG. 14.

As shown in FIG. 17, a loading station 130 may be used to facilitate connection of the pedicle screw PS, the holding assembly 3 (i.e., the lateral implant holder 1 and sleeve 20), the holding sleeve 100 and/or the driving mechanism 150 to one another. As shown in FIG. 17, the loading station 130 preferably includes a base 132 and a sliding shoe 134, the shoe 134 preferably being moveably connected to the base 132. The base 132 may be anchored onto a table (not shown). The base 132 preferably including at least one opening 136, preferably circular with flat portions 136a for receiving the pedicle screw PS. The flat portions 136a are preferably sized and configured to prevent the pedicle screw PS from rotating and/or toggling. With the pedicle screw PS in the base 132, the holding assembly 3 (which may be preassembled) may be attached to the pedicle screw PS. Once the pedicle screw PS and the holding assembly 3 are assembled, the sliding shoe 134 may be moved against the lateral implant holder 1 and/or sleeve 20 to prevent the pedicle screw PS from moving with respect to the holding assembly 3. The holding sleeve 100 and/or the driving mechanism 150 may then be attached to the pedicle screw PS. It should be noted that using the loading station 130 is optional and may not be preferred by some surgeons. For example, the screw PS may be attached to the holding assembly 3 by hand.

Figure 29:
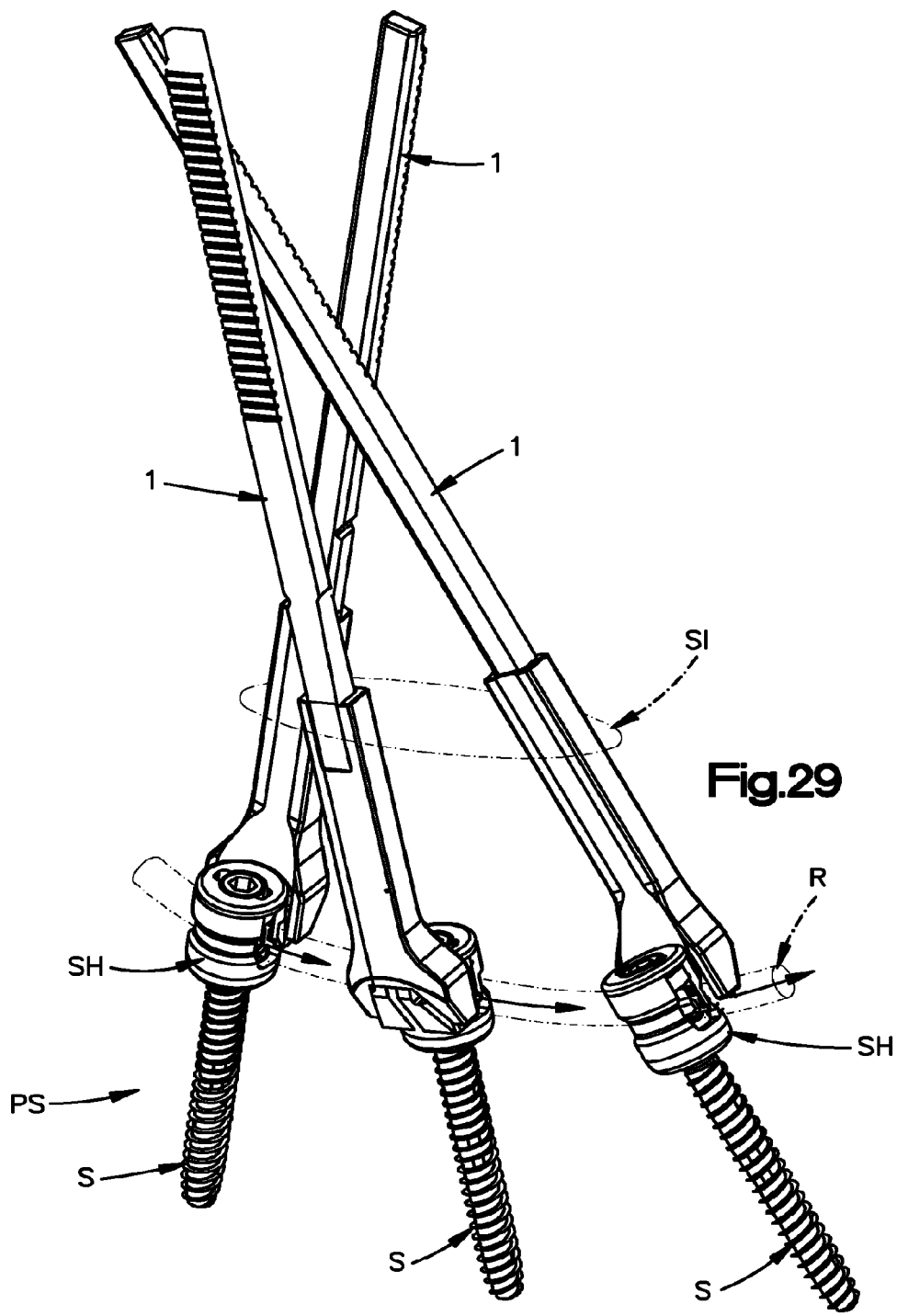
FIG. 29 is a perspective view of three lateral implant holders in accordance with an embodiment of a lateral implant holder attached to pedicle screws as positioned in vertebrae.

Once the holding assembly 3, pedicle screw PS and holding sleeve 100 have been assembled together, the entire construct may be inserted as a single unit into the body through the skin incision SI, preferably until the pedicle screw PS contacts the bone. The driving mechanism 150 may then be inserted through the holding sleeve 100 into engagement with the pedicle screw PS so that the pedicle screw PS may be inserted into the bone. Alternatively, the holding assembly 3, the pedicle screw PS, the holding sleeve 100 and the driving mechanism 150 may all be assemble together and inserted as a single unit into the patient's body through the skin incision SI. When the pedicle screw PS is inserted into the bone, the holding assembly 3 is preferably sized and configured to extend outward from the surgical worksite outside of the skin, thus providing a passageway P (as best shown in FIGS. 26-29) to the surgical worksite and preferably substantially preventing the adjacent tissue from entering the surgical worksite. After the pedicle screw PS is implanted, the holding sleeve 100 and the driving mechanism 150 may then be removed so that the pedicle screw PS and the holding assembly 3 remain in position. The insertion step may be repeated multiple times depending on the procedure to be performed. For example, referring to FIG. 26, a two-level procedure may involve inserting two constructs (i.e., 2 of each of screws and holding assemblies 3). As shown in FIG. 29, a three-level procedure may involve inserting three constructs (i.e., 3 screws PS and holding assemblies 3).

The driving mechanism 150 is preferably used to insert the screw portion S of the pedicle screw PS into the bone. Preferably, the driving mechanism 150 in conjunction with the holding sleeve 100 is sized and configured to prevent rotation and/or toggling of the screw head SH relative to the screw portion S of the pedicle screw. This may be accomplished, for example, by engaging the elongated member 102 with the screw head SH of the pedicle screw PS via the plurality of moveable arms 108, as described above, and by engaging the distal end of the driving mechanism 150 with the screw portion S of the pedicle screw PS. In this manner, the screw head SH of the pedicle screw PS is essentially prevented from toggling with respect to the screw portion S of the pedicle screw PS.

In addition, the interconnecting member 106 may incorporate a ball-detent type mechanism (not shown) for engaging the driving mechanism 150. That is, the throughbore 110 formed in the elongated member 102, handle 104 and interconnecting member 106 of the holding sleeve 100 may contain a ball-detent mechanism in the interconnecting member 106 for engaging the driving mechanism 150. Thus, in use, the driving mechanism 150 is slideably inserted into the throughbore 110 formed in the holding sleeve 100 until the ball-detent mechanism engages the driving mechanism 150. At this point, the surgeon must rotate the driving mechanism 150 and the interconnecting member 106 with respect to the handle 104 and the elongated member 102. Such rotation causes the driving mechanism 150 to advance distally through the throughbore 110 and into engagement with the screw portion S of the pedicle screw PS. As the moveable arms 108 formed on the elongated member 102 engage the inside of the screw head (as previously described) and the driving mechanism 150 engages the head of the screw portion of the pedicle screw PS, the pedicle screw PS is securely engaged (i.e., prohibited from toggling) such that continued rotation of the driving mechanism 150 with respect to the handle 104 will cause the pedicle screw PS to engage the patient's bone.

Figure 18:
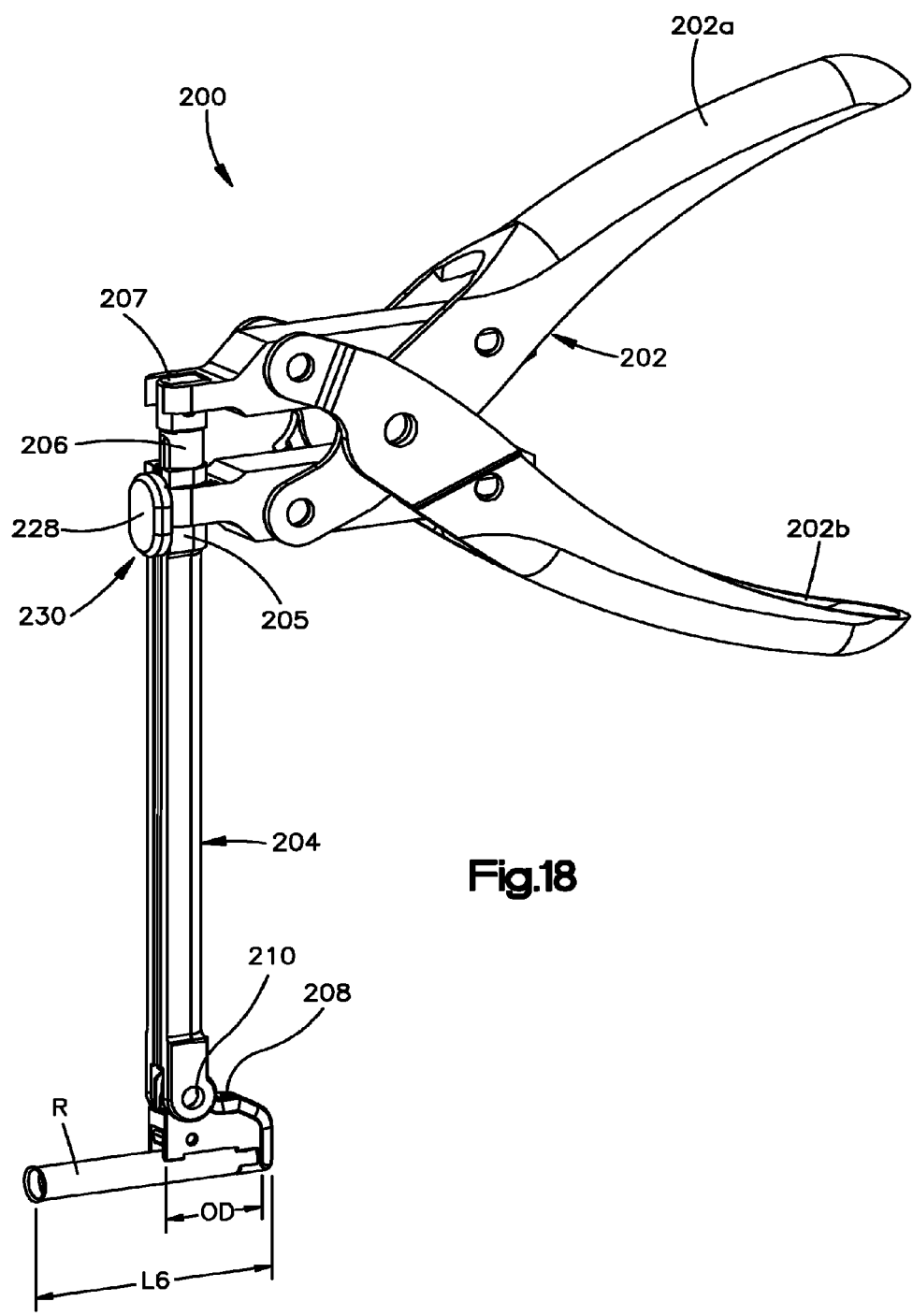
FIG. 18 is a perspective view of an embodiment of a rod holder and a rod.

Referring to FIG. 18, the rod holder 200 may be utilized to insert a rod R down the passageway 31 formed by the tissue protection portion 30 of the holding assembly 3. The rod R may be, by way of non-limiting example, cylindrical or polygonal in shape. The rod R may have a length L5, for example, of between about 20 mm and about 110 mm, more preferably between about 25 mm and about 105 mm and, most preferably, between about 30 mm and about 100 mm and a diameter D3, for example, of between about 3.0 mm, and about 6.5 mm, more preferably between about 4.5 mm and about 6.2 mm and, most preferably, between about 5.5 mm and about 6.0 mm. The size and shape of the rod may be changed or altered depending upon the specific needs, including whether the system us for a one, two, three or more level stabilization. Also, new dynamic or flexible rods may be utilized as well as solid titanium spinal rods as are well known in the art. The rod R may incorporate specific machined geometry to allow loading and/or locking of the rod R onto the rod holder 200. For example, as shown in FIGS. 18-21, the rod R may have a recess 201 to receive a portion (i.e., a protrusion 220) formed on the rod holder 200. The rod R may also incorporate flaring (not shown) of one, or both, ends to enhance the capture of the rod R in the screw heads SH.

The rod holder 200 of FIG. 18 may be used to insert the rod R into the body and, specifically, to insert the rod R into a rod receiving channel formed in the pedicle screws PS. The rod holder 200 may be a passively articulating type rod holder used for initial placement of the spinal rod R into the fixation construct (i.e., the pedicle screw).

As shown in FIG. 18, the rod holder 200 may have a handle 202, an outer elongated member 204, an inner elongated member 206 telescopically located within the outer elongated member 204, and an articulating portion 208. The articulating portion 208 is preferably pivotally connected to the outer elongated member 204 about a pivot 210 so that the articulating portion 208 may be free to move relative to the outer elongated member 204. The handle 202 preferably includes a first arm 202a for connecting to the proximal end 205 of the outer elongated member 204 and a second arm 202b for connecting to the proximal end 207 of the inner elongated member 206. Moreover, the first and second arms 202a, 202b may also include a locking and/or ratchet member (not shown) to fix the positions of the arms 202a, 202b with respect to one another and/or to move the first and second arms 202a, 202b in fixed increments with respect to one another. Movement of the first and second arms 202a, 202b with respect to one another causes the outer elongated member 204 to move (i.e., telescope) with respect to the inner elongated member 206.

The inner elongated member 206 is preferably sized and configured to selectively inhibit movement of the articulating portion 208. That is, the inner elongated member 206 may have a first, static position wherein the inner elongated member 206 is biased away from the articulating portion 208 as shown in FIG. 20, and a second position wherein the inner elongated member 206 may contact the articulating portion 208 as shown in FIG. 21. In order to maintain the inner elongated member 208 in the first position, a biasing member 212 (e.g., a spring) may be located inside the outer elongated member 204 and constructed and arranged to urge the inner elongated member 206 proximally. The biasing member 212 may be operably attached to the outer elongated member 204 and the inner elongated member 206. In the first position, the outer and inner elongated members 204, 206 may be freely pivotable with respect to the articulating portion 208, as illustrated in FIG. 19. When a surgeon desires to fix the orientation of the articulating portion 208, and hence the rod R connected thereto, with respect to the outer and inner elongated members 204, 206 the surgeon may squeeze the first and second arms 202a, 202b of the handle 202, thereby moving the inner elongated member 206 distally against the force of the biasing member 212 such that the inner elongate member 206 may contact a surface 218 of the articulating portion 208. In an alternative embodiment, the biasing member 212 may be constructed and arranged to bias the inner elongated member 206 distally so that the inner elongated member 206 contacts the articulating portion 208. In order to disengage the inner elongated member 206 from the articulating portion 208, the handle 202 may be configured such that squeezing the handle 202 moves the inner elongated member 206 proximally, away from the surface 218 of the articulating portion 208, thereby allowing the articulating portion 208 to move relative to the outer elongated member 204.

The handle 202 may provide variable braking of the articulating portion 208 ranging from relatively low, constant drag braking to significantly rigid locking of the articulating portion 208. This may provide the surgeon with control over the degree of hinge articulation and, therefore, rod angle 0 which may be, for example, between +30 degrees and about −120 degrees, more preferably between about +20 degrees and about −110 degrees and, most preferably, between about +10 degrees and about −90 degrees.

The articulating portion 208 may also include an engagement device 219 which may secure the rod R to the rod holder 200. That is, the rod R may be loaded into the rod holder 200 so that the proximal portion 221 of the rod R may be positioned in an opening 222 of the articulating portion 208 and the protrusion 220 formed on the engagement device 219 is positioned in the recess 201 formed on the rod R as shown, for example, in FIG. 19. The protrusion 220 of the engagement device 219 may be biased into the recess 201 of the rod R by a biasing member 224 (e.g., a spring). The engagement device 219 may be pivotally connected to the articulating portion 208 at a pivot point 219a. In order to disengage the rod R from the rod holder 200, the engagement device 219 may be pivoted so that the protrusion 220 disengages from the recess 201 formed in the rod R. In order to accomplish this, the rod holder 200 may include a shaft 226 positioned inside or outside (e.g., in a groove) of the outer elongated member 204.

The shaft 226 may include a drive portion 228 (e.g., a button) positioned, for example, at its proximal end 230 so that the surgeon may control movement of the shaft 226 relative to the outer elongated member 204. Those skilled in the art will appreciate that the drive portion 228 may be a separate piece from the shaft 226. Alternatively the drive portion 228 may be an integral portion of the shaft 226. In use, the surgeon may push the drive portion 228 distally, towards the articulating portion 208, to cause the shaft 226 to move towards the distal end 219b of the engagement device 219. As illustrated in FIG. 19, when the outer elongated member 204 is at an angle less than 90 degrees with respect to the articulating portion 208, the shaft 226 may be prevented from moving past the articulating portion 208. However, when the shaft 226 is aligned with a passageway or groove 232 formed on the articulating portion 208, the shaft 226 may be moveable between the position shown in FIG. 20 and the position shown in FIG. 21. As the shaft 226 moves distally, the shaft 226 may pass through the passageway or groove 232 formed in the articulating portion 208 so that the distal end 234 of the shaft 226 may depress the distal end 219b of the engagement device 219, thereby causing the proximal end 219c of the engagement device 219 to assert a force against the biasing member 224, in turn, causing the protrusion 220 formed on engagement device 219 to move out of the recess 201 formed on the rod R, which in turn causes the rod R to be disengaged from the rod holder 200. The rod holder 200 may then be removed from the body, leaving the rod R in the screw head SH. It is envisioned that any means of engaging and disengaging the rod R may be used. As best shown in FIG. 19, the articulating portion 208 may be sized so that the articulating portion 208 has an outermost dimension OD which is substantially the same or less than the length L6 of the rod R. Such a configuration may allow the articulating portion 208 to pass through the screw head SH and, in particular, the U-shaped channel formed in the screw head SH.

Alternate preferred embodiments of the rod holder are illustrated in FIGS. 22-25C. As shown, the rod holder 250 may include an elongated member or housing 252 containing a shaft 254, a rod receiving assembly 260 which is preferably operably associated with the elongated member 252 and/or the shaft 254, a bar 262, and a handle assembly 270 having first and second handles 270a, 270b. The first and second handles 270a, 270b are interconnected via a pivot 271. Furthermore, as shown, preferably the first handle 270a is connected to the shaft 254 while the second handle 270b is connected to the elongated member 252 so that movement of the first and second handles 270a, 270b with respect to each other causes the shaft 254 to move with respect to the elongated member 252.

Figure 22:
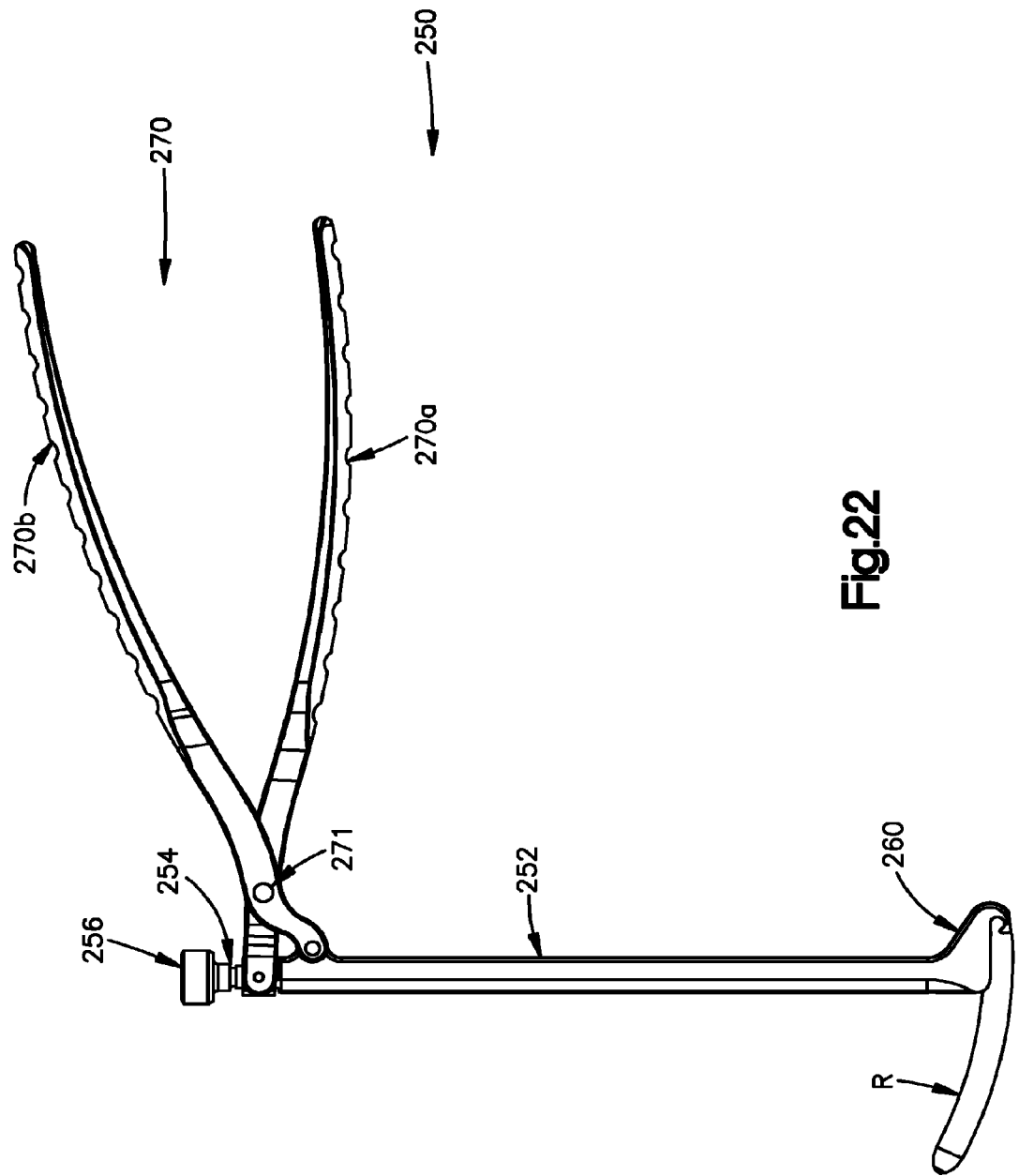
FIG. 22 is a side elevational view of an embodiment of a rod holder.

As best shown in FIG. 22, the shaft 254 preferably includes a threaded portion (not shown) located at the proximal end thereof for engaging a threaded bore (not shown) formed in the first handle 270a. The shaft 254 also preferably includes a knob 256 located on the proximal end thereof for facilitating rotation of the shaft 254 with respect to the elongated member 252 so that rotation of the knob 256 and/or the shaft 254 with respect to the elongated member 252, as a result of the corresponding threaded portions, causes the shaft 254 to move with respect to the elongated member 252.

Referring to FIGS. 23-25C, the rod receiving assembly 260 preferably includes an aperture or hook portion 264 for receiving the rod R, preferably an end of the rod R, and at least one displaceable bar 262. The rod receiving assembly 260 is preferably integral with the elongated member or housing 252. Accordingly, when the shaft 254 is disengaged from the bar 262, as best shown in FIG. 23, the rod R is freely insertable and removable from the aperture 264 of the rod holder 250. Alternatively, the shaft 254 may be urged towards the bar 262 thus requiring the user to move the shaft 254 away from the bar 262 before the rod R can be inserted into the aperture 264 of the rod holder 250. As shown, preferably the distal end of the bar 262 contains a surface sized and configured to substantially match the sized and contour of the outer surface of the rod R. Moreover, preferably the rod receiving assembly 260 is sized and configured so that the bar 262 and other associated components are maintained within the rod holder 250 and thus prohibited from coming free.

In use, once the surgeon has inserted the rod R into the aperture 264 of the rod holder 250, the surgeon rotates the shaft 254 and/or the knob 256 which causes the shaft 254 to move distally with respect to the elongated member 252 and thus causes the shaft 254 to contact the bar 262, which in turn presses the bar 262 against the rod R which has been inserted into the aperture 264. The rod R is thereby retained and coupled to the rod holder 250 but can articulate or rotate with respect to the rod holder 250. The pressing of the bar 262 against the rod R may provide a sufficient amount of frictional force and/or contact between the rod R and the bar 262 to cause the rod R to be retained within the aperture 264 of the rod holder 250. Alternatively, the shaft 254 may simply move the bar 262 and/or retain it in position so that there is insufficient clearance to remove the end of the rod R from the aperture 264. However, at this point, the rod R is still free to move (i.e., articulate and/or pivot) with respect to the rod holder 250. That is, once the rod R has been properly inserted into the rod holder 250, rotating the shaft 254 and/or the knob 256 causes the rod R to be retained within the aperture 264 of the rod holder 250 but still permits the rod R to articulate with respect to the rod holder 250. As would be appreciated by one of ordinary skill in the art, to remove (i.e., disengage) the rod R from the rod holder 250, the surgeon needs to rotate the shaft 254 and/or the knob 256 in the opposite direction. Thus, rotation of the shaft 254 and/or the knob 256 causes the rod R to be retained and/or released from the rod holder 250.

To prevent the rod R from articulating with respect to the aperture 264, the surgeon moves the first and second handles 270a, 270b toward each other, which in turn causes the shaft 252 to move an additional distance with respect to the elongated member 252. This additional movement, in turn, causes the shaft 254 to apply additional force onto the bar 262, which causes the bar 262 to apply an additional braking force against the rod R, which permits the surgeon, depending upon the force applied to the handles 270a, 270b, to vary the force applied to the rod R and thus control the angular position of the rod R with respect to the rod holder, and if enough force is applied results in the position of the rod R being fixed with respect to the rod holder 250. Thus, squeezing the first and second handles 270a, 270b may cause the articulated position of the rod R to be fixed with respect to the rod holder 250.

Figure 25A:
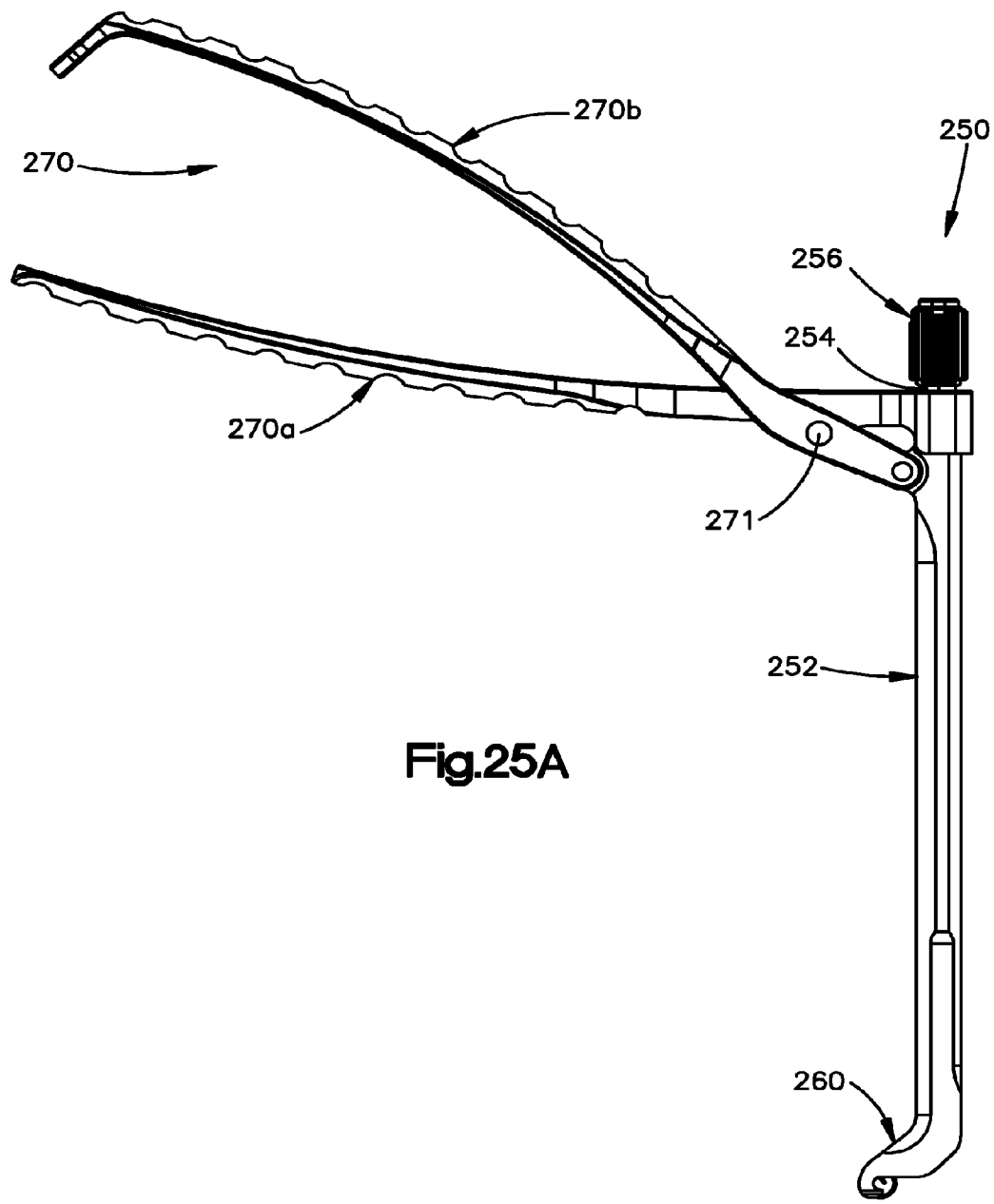
FIG. 25A is a side elevational view of an embodiment of a rod holder.
Figure 27:
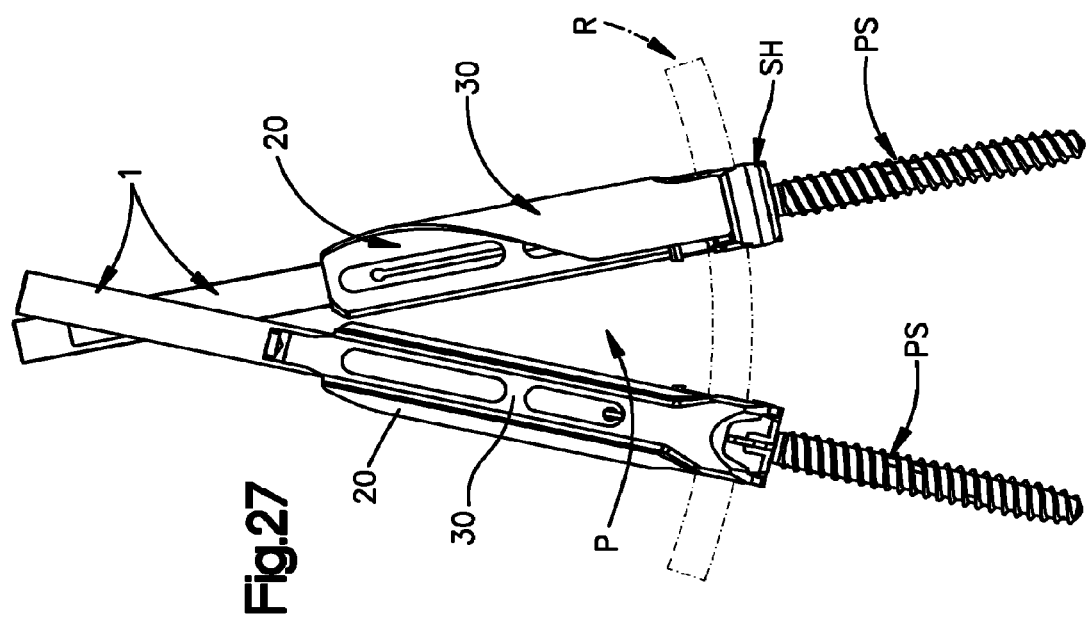
FIG. 27 is a side view of the assembly FIG. 26.

As best shown in FIGS. 25B and 25C, the rod receiving assembly 260 may also include a slot 266 proximate to the aperture 264. The rod R may preferably include a narrow end Ra and a pair of projections Rb. Preferably, the narrow end Ra may be received in the slot 266 and the projections Rb may be received in the aperture 264. By way of a non-limiting example, the rod R may be a rod referred to in the art as an atraumatic bullet-nosed rod.

It is to be understood that other variations of the rod holder are contemplated, such as incorporating a bushing 268 and/or a retaining projection in the rod receiving assembly 260.

Figure 30:
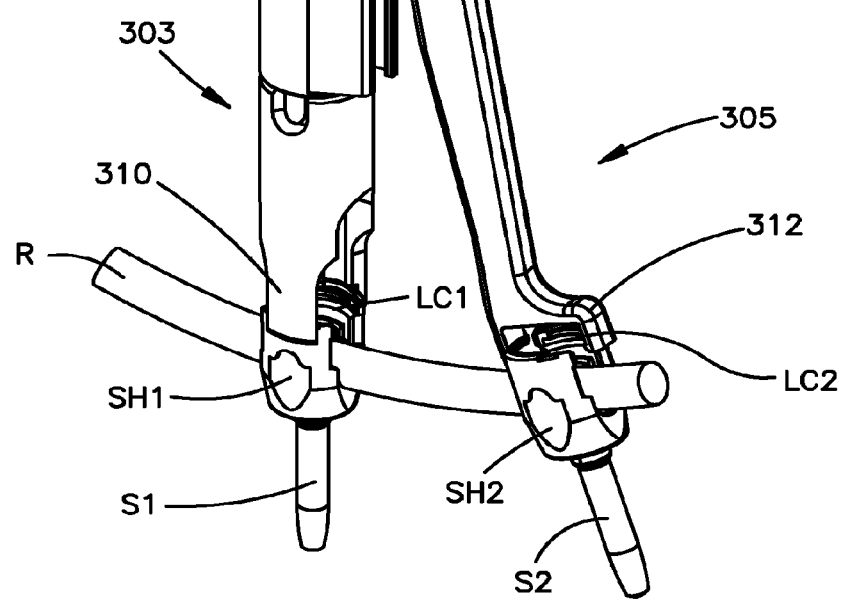
FIG. 30 is a perspective view of an embodiment of a compressor assembly.
Figure 31:
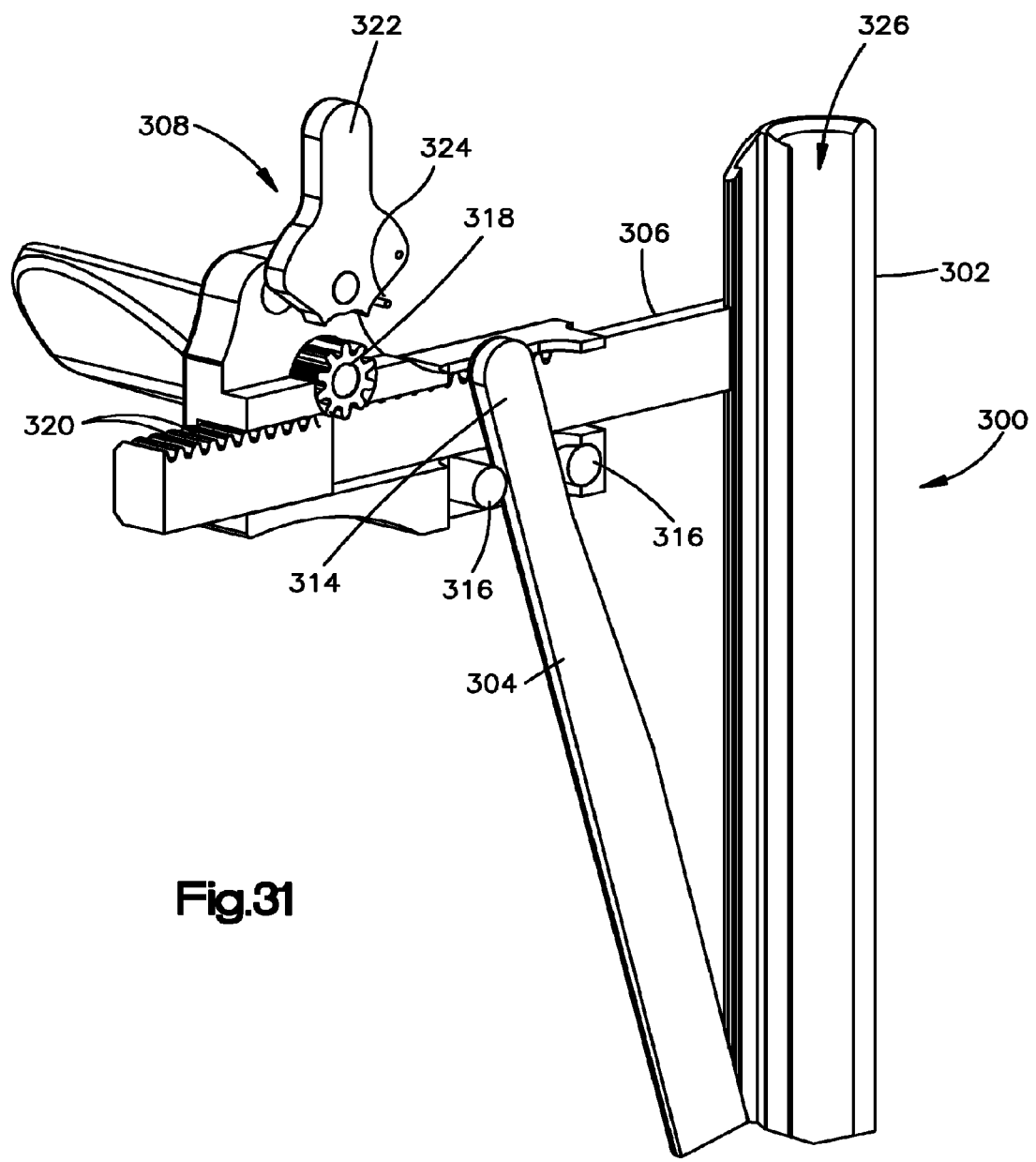
FIG. 31 is a cross-sectional view of a portion of the compressor assembly of FIG. 30.

Once the rod R is positioned in the screw heads SH, a movement mechanism 300, such as a compressor and/or distractor, may be used to move one pedicle screw PS with respect to another pedicle screw PS, and hence to move one vertebrae V1 (not shown) with respect to another vertebrae V2 (i.e., to compress or distract vertebrae V). As illustrated in FIGS. 30-31, the compressor/distractor 300 may include a first member 302 which engages a first screw S1, a second member 304 which preferably is pivotally attached to the first member 302 and which engages a second screw S2, and an actuation mechanism 308 connected to the first and second members 302, 304 for moving the second member 304 relative to the first member 302. As shown, the compressor/distractor 300 may also include a bar 306 extending from the first member 302. The bar 306 being sized and configured to receive the actuation member 308. As shown, preferably, the bar 306 and actuation mechanism 308 form a rack and pinion type connection to facilitate movement of the second member 304 with respect to the first member 302 and hence to move one vertebrae V1 with respect to another vertebrae V2.

A first set screw or locking cap LC1 may engage the first screw head SH1 of the first screw S1 so that the rod R is captured within the rod receiving channel formed in the pedicle screw PS. However at this point, the rod R is still free to move axially with respect to the first screw S1. A second set screw or locking cap LC2 may engage the second screw head SH2 and may be tightened against the rod R so that the rod R may be fixed with respect to the second screw S2. Alternatively, the first set screw or locking cap LC1 may engage the first screw head SH1 of the first screw S1 and may be tightened against the rod R so that the rod R may be fixed with respect to the first screw and the second set screw or locking cap LC2 may engage the second screw head SH2 so that the rod R may be moveable relative to the second screw S1. The distal end 303 of the first member 302 preferably includes a first contact member 310 sized and configured to receive the first locking cap LC1 and the first screw head SH1. The distal end 305 of the second member 304 may likewise include a second contact member 312 sized and configured to receive the second locking cap LC2 and the second screw head SH2.

As shown in FIG. 31, the actuation mechanism 308 is preferably sized and configured to receive a portion of the proximal end 314 of the second member 304 so that the second member 304 may be free to move, and more preferably rotate, relative to the actuation mechanism 308. For example, the actuation member 308 may include a plurality of prongs 316 and the proximal end 314 of the second member 304 may be sized and configured to be positioned between the prongs 316. Other means of pivotally interconnecting the second member 304 to the actuation mechanism 308 are also envisioned such as, for example, connecting the proximal end 314 of the second member 304 to the actuation mechanism 308 via a pivot point.

The actuation mechanism 308 may include a gear 318 sized and configured to engage teeth 320 formed on the bar 306. A knob 322 may be used to rotate the gear 318 so that rotation of the knob 322 causes the actuation mechanism 308 to move along the bar 306. The actuation mechanism 308 may also include a locking mechanism 324 to prevent the actuation mechanism 308 from moving relative to the bar 306, thus preventing the displacement of the second member 304 relative to the first member 302. Consequently, the first and second screw S1, S2 may be maintained stationary relative to each other. In an alternate configuration, the locking mechanism 324 may retain the gear 318 in position to prevent the gear 318 from rotating.

Movement of the first screw S1, and hence vertebrae V1, with respect to the second screw S2, and hence vertebrae V2, may be achieved my moving the actuation mechanism 308 along the bar 306. That is, moving the actuation mechanism 308 towards the first member 302 may cause distraction (i.e. the first and second screws S1, S2 separate or move apart from one another), thereby causing vertebrae V1, V2 to move away from each other. Alternatively, moving the actuation mechanism 308 away from the first member 302 may cause compression (i.e., the first and second screws S1, S2 may move toward each other), thereby causing vertebrae V1, V2 to move toward each other. Once the vertebrae V1, V2 have been compressed and/or distracted and the locking mechanism 324 has been engaged so that the position of screws S1, S2 (and vertebrae V1, V2) are maintained in a fixed position with respect to one another, a locking tool, such as but not limited to a screwdriver, etc. (not shown) may be inserted through the passageway 326 in the first member 302 to tighten the set screw or locking cap LC1 of the first screw S1 to the rod R, thereby fixing the rod R to the first screw S1 and maintaining the position of the first screw S1 with respect to the second screw S2.

FIG. 32 illustrates an alternative movement mechanism (i.e., compressor) 400, which may be used for compression. Similar to the previously embodiment discussed above, the movement mechanism 400 may include a first member 402 which may engage a first screw S1, a second member 404 which may engage a second screw S2, an actuation mechanism 403 and, a third member 408 connecting the second member 404 and the actuation mechanism 403. The second and third members 404, 408 may be pivotally connected to the first member 402. As shown, preferably, in this embodiment, the actuation mechanism 403 includes a bar 406 extending from the first member 402.

A surgeon may provisionally tighten a set screw or locking cap LC1 on the first screw S1 so that the rod R may be captured within the rod receiving channel formed in the first screw S1. However at this point, the rod R is still free to move axially with respect to the first screw S1. Moreover, the surgeon may tighten a set screw or locking cap LC2 to the second screw S2 so that the rod R maybe fixed relative to the second screw S2. As shown in FIG. 32, the surgeon may position the second member 404 proximate the side 410 of the second screw S2 farthest away from the first screw S1.

The third member 408 may be moveably attached to the bar 406, which preferably incorporates threads 412 formed thereon. For example, the third member 408 may have an opening 414 for receiving the bar 406. A surgeon may move the third member 408, via the actuation mechanism 403, towards the first member 402, whereupon the distal end 416 of the third member 408 moves away from the first member 402 causing the proximal end 418 of the second member 404 to move away from the first member 402, resulting in the distal end 420 of the second member 404 to moves towards the first member 402 so that the second member 404 may apply a force on the side 410 of the second screw S2 causing the first screw S1 to move toward the second screw S2, and hence causing the first vertebra V1 (not shown) to move toward the second vertebra V2 (not shown). That is, since the second screw S2 is tightened to the rod R, the first screw S1, and hence vertebra V1 attached thereto, will move towards the second screw S2 thereby compressing vertebrae V1, V2. When the vertebrae V1, V2 are compressed a desired amount, an optional locking nut 422 may be moved (e.g., rotated) along the bar 406 and positioned against the third member 408. In turn, the locking nut 422 will fix the position of the first and second members 402, 404 and, consequently, the first and second vertebrae V1, V2 relative to one another. With the first and second vertebrae V1, V2 fixed with respect to one another, a locking tool, such as but not limited to a screwdriver, (not shown) may be inserted down the passageway 424 of the first member 402 to tighten the loose set screw/locking cap LC1 so that the first screw S1 may be fixed with respect to the rod R. After tightening the set screw LC1, the movement mechanism 400 may be released and removed from the skin incision SI. Those skilled in the art will appreciate that the movement mechanism 400 may also be configured to distract vertebrae V1, V2 as well.

An example of a fixation procedure utilizing an embodiment of the system will now be described. In use, for a one-level procedure (i.e., a procedure involving two screws and two vertebrae), a surgeon may make a single incision having a length of, for example, between about 15 mm and about 50 mm and, more preferably between about 20 mm and about 40 mm and, most preferably, between about 25 mm and about 35 mm. The incision may also, for example, be between about 0 mm to 50 mm, more preferably between about 20 mm and about 40 mm and, most preferably, between about 25 cm and about 30 cm lateral to the midline. The desired skin incision length may vary according to the patient anatomy. The incision length may increase as the incision extends deeper into the body and preferably ends proximate the muscle, so that the muscle tissues are not torn. For example, the length of the incision proximate the muscle tissue may be between about 45 and 50 mm. The muscle tissue may be displaced to expose the surgery worksite, preferably approximately the same length as the incision length proximate the muscle tissue. By way of non-limiting example, the muscle tissue may be pushed aside to expose the bone.

The incision may be made in the posterior spine and may be dilated down to the vertebrae by, for example, blunt dilation preferably between the multi fidus and longissimus muscle planes with a finger or with a blunt dilator or other instrument down to the bone. A larger incision may be necessary for a two or more level procedure. The surgeon may locate and prepare for inserting the pedicle screw PS by using, for example, x-rays, fluoroscopic observation, etc. A guide wire (e.g., K-wire) may be inserted into one or more vertebrae and the procedure may be performed over the guide wire anchored in the pedicle.

The holding assembly 3 (i.e., the lateral implant holder 1 and sleeve 20) may be attached to the screw head SH of the pedicle screw PS prior to screw placement, more preferably prior to making the skin incision SI. The sleeve 20 is preferably in the opened position as shown in FIG. 3 and the first and second jaw members 8a, 8b of the lateral implant holder 1 may be placed around the screw head SH. Thereafter, the sleeve 20 may be moved to a closed position as shown in FIG. 4, thereby preventing the lateral implant holder 1 from separating from the screw head SH. The assembly of the lateral implant holder 1, the sleeve 20 and the pedicle screw PS may be accomplished, if so desired, using the loading station 130, as described in connection with FIG. 17. Once the lateral implant holder 1, the sleeve 20 and the pedicle screw PS are assembled, the holding sleeve 100, such as the embodiment shown in FIGS. 14-17 may be attached thereto. The embodiment of the sleeve 20 to be used, more specifically, the embodiment of the tissue protection portion 30 to be used in the procedure may be selected depending on the type, level, and location of the procedure. For example, two right-handed sleeves may be desirable for a procedure on the left side of the patient, whereas two left-handed sleeves may be desirable for a procedure on the right side of the patient.

It should be noted that the use of the tissue protection portions 30 is optional and may be dependent on the procedure being performed and the preference of the surgeon. Sleeves 20 without a tissue protection portion 30 may be used by surgeons who do not require tissue protection portions 30 and/or by surgeons who may want to reduce the size of the skin incision SI (and muscle retraction) for a given size fixation construct. As such, the fixation construct may be created with any combination of tissue protection portions 30, or alternatively, without any tissue protection portion 30, based on the surgeon's preference.

The elongated member 102 of the holding sleeve 100 may be inserted through the passageway 31, P formed by the tissue protection portions 30 of the sleeve 20 so that the distal end 108 of the elongated member 102 is positioned in the screw head SH. Preferably, the distal end 108 of the elongated member 102 is sized and configured to prevent the screw head SH of the pedicle screw PS from moving relative to the lateral implant holder 1 and sleeve 20. The handle 104 of the holding sleeve 100 may be sized and configured to receive the lateral implant holder 1 so that the surgeon may grasp the handle 104 to insert the construct (i.e., the lateral implant holder 1, the sleeve 20, the pedicle screw PS and the holding sleeve 100) into the body and/or to insert the pedicle screw PS into the patient's bone. A driving mechanism 150, such as a screw driver, may be positioned in the throughbore 110 formed in the holding sleeve 100 so that the distal end of the driving mechanism 150 engages the screw portion S of the pedicle screw. The lateral implant holder 1, the sleeve 20, the pedicle screw PS and the holding sleeve 100 may be positioned through the skin incision SI and into the body as a single unit/construct. The driving mechanism 150 may be inserted at the same time as the construct or may be inserted into the body once the construct is positioned in the body.

The driving mechanism 150 may be used to insert the screw portion S of the pedicle screw PS into the bone. Specifically, while a surgeon holds the handle 104 of the holding sleeve 100, the driving mechanism 150 may be rotated to insert the screw portion S of the pedicle screw into the bone, preferably a vertebra. Once the pedicle screw PS is implanted into the bone, the driving mechanism 150 and/or the holding sleeve 100 may be removed from the lateral implant holder 1 and sleeve 20. To disengage the holding sleeve 100 from the holding assembly 3, and specifically from the lateral implant holder 1, the surgeon may depress pushbutton 112 of the holding sleeve 100. The holding assembly 3 may remain partially in the body so that the tissue protection portion 30 extends out of the body and through the skin incision SI, preferably preventing the displaced tissue (i.e., muscle, skin) from closing in above the pedicle screw PS. The holding assembly 3 may provide a means for screw head manipulation, a visual indication of screw location and orientation, and a mounting structure for introducing additional instruments for the procedure. The procedure may be repeated through the skin incision SI numerous times to allow a surgeon to implant additional pedicle screws PS preferably into different bones, each time inserting a holding assembly 3 into the body.

The surgeon may implant the pedicle screws PS with adjacent holding assemblies 3 in a staggered orientation (medial-lateral for a 1-level construction, comprising two screws PS medial-lateral-medial for a 2-level construction comprising three pedicle screws PS) along the length of the fixation construct. Once the pedicle screw PS have been inserted into the bone, an instrument may be used to measure the distance between pedicle screws PS to determine the length of the rod R to be used for fixation. Preferably, the holding assemblies 3 may be configured so that when implanted in an alternating (medial-lateral) pattern the portions extending above the skin incision SI do not interfere (or minimally interfere) with each other. Preferably, the helices of the sleeve 20 are constructed and arranged so as to reduce or eliminate interference between adjacent sleeves 20 and/or lateral implant holders 1, and more preferably to intermesh together. Significantly curved (lordosed) patient lumbar geometries may therefore be accommodated without interference of the lateral implant holder 1 or tissue protection portion 30. Moreover, as best illustrated in FIG. 28, the intermeshing tissue protection portions 30 of the sleeves 20 may create a passageway P (e.g., a channel) for guiding the rod R into contact with and preferably for reception by the screw heads SH. The passageway P may provide a path for rod placement, visualization of the tops of the screw heads and instrument access to the tops of the screw heads.

With the pedicle screws PS inserted into the bone and the holding assembly 3 still retaining the pedicle screws PS, the surgeon may place the rod R through the passageway P created by the tissue protection portions 30 of the sleeves 20. The rod R is inserted into the surgery worksite preferably using a rod holder, which may, for example, be fixed (e.g., forceps) or have an articulating or adjustable portion (e.g., rod holder 200, 250). The rod R may be placed into the body and through the passageway P created by the tissue protection portions 30 of the sleeve 20 in an orientation which may be non-horizontal, vertical, oblique or substantially perpendicular to the spine. Preferably, the rod R is substantially parallel to the lateral implant holder 1 as rod R is being inserted into the body. As the rod R passes through the skin incision SI into the body, or after the rod R is brought proximate the screw head SH, the rod R may be aligned with the screw heads SH and seated therein. Preferably, the rod R is rotated from a substantially parallel position to a substantially perpendicular position with respect to the lateral implant holder 1. Preferably, the rod R can rotate about the aperture, for example, between about +30 degrees proximally to about −120 degrees distally and, more preferably, about +20 degrees proximally and about −110 degrees distally and, most preferably, between about +10 degrees proximally and about −90 degrees distally.

In a procedure using, for example, a rod holder and an atraumatic bullet-nosed rod, the rod R may be attached to the rod holder by inserting the narrow end Ra of the rod R into a slot formed in the rod holder such that projections Rb formed on the rod R are received in an aperture formed on the receiving assembly. The rod holder may contain a moveable mechanism to contact and to apply a series of pressures on the rod R so that the rod R may be secured and/or fixed with respect to the rod holder.

In an embodiment where the rod R has a flared portion and the embodiment of rod holder 200 shown in FIG. 18 is utilized, the rod R may be positioned through the channel C in the screw head SH so that the flared portion of the rod R may engage the outer surface of the screw head SH. The flared portion may be pulled back until the flared portion engages the outer surface of the screw head SH so that the rod R cannot be pulled through the screw head SH (i.e., so that the flared portion is kept in contact with the screw head SH). With the flared portion positioned snugly against the screw head SH, the rod R can be rotated until the rod R is positioned in all the desired screw heads SH.

The surgeon may squeeze the handle of the rod holder to control the angulation of the rod R relative to the rod holder. After the rod R is positioned in all the screw heads, locking caps and/or set screws may be positioned in the screw heads SH over the rod R to fix the rod R with respect to the pedicle screws PS. The rod R may be released from the rod holder and the rod holder may then be removed from the body. It should be noted that the rod holder may be removed from the body before the locking caps and/or set screws are positioned in the screw heads SH. If preferred, a rod persuader (not shown) may be used to facilitate seating the rod R into the screw heads SH.

If compression/distraction of the vertebrae is desired, a movement mechanism may be used to compress/distract the vertebrae. The surgeon may insert the movement mechanism through the passageway 31, P created by the tissue protection portions of the sleeve. As previously described, a surgeon may attach a first member via a first contact member to a first pedicle screw S1, the first screw S1 preferably having a locking cap or set screw LC1 provisionally affixed thereto. The surgeon may attach a second member via a second contact member to a second pedicle screw S2, the second screw S2 having a completely tightened locking cap or set screw LC2. In accordance with an embodiment of locking cap or set screw LC1, LC2, the locking cap or set screw may include a threaded portion to screw into the locked position. Alternatively, the locking cap and/or set screw LC1, LC2 may snap into the screw head SH and be rotated into the locked position.

In the embodiment shown in FIG. 30, the knob may be turned so that the actuation mechanism may move along the bar. In the embodiment shown in FIG. 32, the first and third members may be moved towards each other. As the actuation member moves toward the first member, the first screw S1 may move away from the second screw, thereby resulting in distraction of the vertebrae V1 and V2. As the actuation member and third member move away the first member, the first screw S1 may move toward the second screw S2, thereby resulting in compression of the vertebrae V1 and V2. Once the vertebrae and screws are in the desired position, the locking cap and/or set screw may be engaged to prevent further movement of the screws, and hence the vertebrae, relative to each other. A tool (not shown) may be inserted down the first member and may be used to fully tighten the locking cap and/or set screw of the first screw S1. With the fixation construct in place, the movement mechanism and the holding assembly 3 may be removed from the body and the skin incision SI may be closed.

Although the invention and its advantages have been described in detail, it should be understood that various changes, substitutions, and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, composition of matter, means, methods, or steps, presently existing or later to be developed that perform substantially the same function or achieve substantially the same result as the corresponding embodiments described herein may be utilized according to the present invention.

It will be appreciated by those skilled in the art that various modifications and alterations of the invention can be made without departing from the broad scope of the appended claims. Some of these have been discussed above and others will be apparent to those skilled in the art.

What is claimed is:

1. A minimally invasive fixation system comprising:
 a tissue protection portion configured to be mounted to a bone anchor, the tissue protection portion comprising a proximal end, a distal end spaced from the proximal end along an axis that is oriented along a direction, and a wall that extends along the axis from the proximal end to the distal end, the wall defining an outer perimeter that extends about the axis along a plane that is normal to the axis, wherein the wall has a proximal portion and a distal portion spaced from the proximal portion along the axis, such that the distal portion of the wall terminates at the distal end of the tissue protection portion with respect to the direction,
 wherein 1) at an entirety of the distal portion, the outer perimeter extends about the axis a first distance, such that at no location at the proximal portion does the outer perimeter extend about the central axis a distance that is greater than or equal to the first distance, 2) the outer perimeter does not extend completely about the axis at the proximal portion, and 3) the outer perimeter does not extend completely about the axis at the distal portion.

2. The minimally invasive fixation system of claim 1, wherein the tissue protection portion is a first tissue protection portion, the wall is a first wall, the axis is a first axis, the passageway is a first passageway, the proximal portion is a first proximal portion, the distal portion is a first distal portion, the bone anchor is a first bone anchor, and the direction is a first direction, the minimally invasive fixation system further comprising:
 a second tissue protection portion configured to be mounted to a second bone anchor, the second tissue protection portion comprising a second wall.

3. The minimally invasive fixation system of claim 2, wherein the second wall has a second proximal portion and a second distal portion, the second wall defines a second axis that extends along a second direction from the second proximal portion to the second distal portion, the second wall extends around the second axis to define a second passageway, and the second proximal portion does not extend as far around the second axis as the second distal portion.

4. The minimally invasive fixation system of claim 3, wherein the second direction is opposite to the first direction.

5. The minimally invasive fixation system of claim 3, wherein:
 the first distal portion extends around the first axis between about 250 degrees to about 300 degrees, and
 the second distal portion extends around the second axis between about 250 degrees to about 300 degrees.

6. The minimally invasive fixation system of claim 5, wherein the first and second distal portions each extend about 270 degrees around the first and second axes, respectively.

7. The minimally invasive fixation system of claim 5, wherein the first and second walls each define an edge, a portion of the edge being inclined with respect to the first and second axes, respectively, wherein the first and second walls transition from the first and second proximal portions, respectively, to an intermediate point via the respective inclined portions of each edge.

8. The minimally invasive fixation system of claim 2, wherein the first tissue protection portion is configured to be attached to a first implant holder, and the second tissue protection portion is configured to be attached to a second implant holder, each of the first and second implant holders having a distal end sized and configured to selectively receive at least one of the first and second bone anchors.

9. The minimally invasive fixation system of claim 2, further comprising a holding sleeve including a handle and an elongated member, wherein the elongated member has a distal end constructed and arranged to selectively contact one of the first and second bone anchors such that the contacted bone anchor is not pivotable relative to the respective tissue protection portion.

10. The minimally invasive fixation system of claim 9, wherein the elongated member has a passageway therethrough, the passageway of the elongated member being sized and configured to receive a driving mechanism, the driving mechanism being constructed and arranged to engage the contacted bone anchor to drive the contacted bone anchor into the bone.

11. The minimally invasive fixation system of claim 2, further comprising a movement mechanism configured to move the first bone anchor relative to the second bone anchor.

12. The minimally invasive fixation system of claim 11, wherein the movement mechanism has a first member configured to contact the first bone anchor, a second member configured to contact the second bone anchor, and a bar extending from the first member, the second member being displaceable relative to the bar, wherein displacement of the second member relative to the bar results in displacement of the second member relative to the first member.

13. The minimally invasive fixation system of claim 12, wherein the movement mechanism further comprises an actuation mechanism constructed and arranged to move along the bar, the actuation mechanism being operably associated with the second member and the bar to move the second member as the actuation mechanism moves along the bar.

14. The minimally invasive fixation system of claim 13, wherein the bar has teeth and the actuation mechanism has a knob and a gear, the knob contacting the gear, and the gear contacting the teeth such that rotation of the knob moves the gear along the teeth.

15. The minimally invasive fixation system of claim 13, wherein the second member is shaped so that movement of the actuation mechanism toward the first member causes the first and second bone anchors to move apart, and movement of the actuation mechanism away from the first member causes the first and second bone anchors to move together.

16. The minimally invasive fixation system of claim 12, wherein the movement mechanism further comprises a third member operably associated with the second member, the second and third members constructed and arranged such that movement of the third member towards the first member causes a distal end of the second member to move towards the first member.

17. The minimally invasive fixation system of claim 16, wherein the second and third members are pivotally coupled to the first member.

18. The minimally invasive fixation system of claim 2, wherein the first wall comprises a first edge extending helically around the first axis from the first proximal portion toward the first distal portion.

19. The minimally invasive fixation system of claim 18, wherein the second wall comprises a second edge extending helically around the second axis in a direction from the second proximal portion toward the second distal portion.

20. The minimally invasive fixation system of claim 19, wherein the first and second edges are sized and configured to permit the first and second tissue protection portions to intermesh so that an opening is defined between the first and second walls to allow a rod to be inserted through the opening and mounted on the first and second bone anchors.

21. The minimally invasive fixation system of claim 2, further comprising the second bone anchor connected to the second tissue protection portion.

22. The minimally invasive fixation system of claim 2, further comprising a rod configured to be mounted onto the first and second bone anchors in an opening defined between the first and second walls.

23. The minimally invasive fixation system of claim 1, further comprising a rod holder having an elongated body, a shaft housed within the elongated body, and a retaining assembly constructed and arranged to selectively retain a rod, wherein the shaft is displaceable between a first position wherein the rod is retained and a second position wherein the rod is released.

24. The minimally invasive fixation system of claim 23, wherein the retaining assembly includes a displaceable bar, wherein the shaft pushes the bar toward the rod such that the bar contacts the rod when the shaft is in the first position.

25. The minimally invasive fixation system of claim 23, wherein the rod holder further includes a handle constructed and arranged to move the shaft between the first position and the second position.

26. The minimally invasive fixation system of claim 23, wherein the rod holder further includes a handle having a first member attached to the shaft and a second member attached to the elongated body, such that displacement of the first member with respect to the second member selectively moves the shaft between the first position and the second position.

27. The minimally invasive fixation system of claim 23, wherein the retaining assembly includes a slot, wherein the rod includes an end portion constructed and arranged to be received by the slot.

28. The minimally invasive fixation system of claim 23, further comprising the rod, wherein the rod includes a projection and the retaining assembly includes an aperture configured to receive the projection.

29. The minimally invasive fixation system of claim 1, further comprising a rod holder comprising an elongated body operably associated with an articulating portion, the articulating portion pivotally connected to the elongated body, the articulating portion constructed and arranged to engage a rod.

30. The minimally invasive fixation system of claim 29, wherein the elongated body of the rod holder has an outer elongated member and an inner elongated member moveable relative to the outer elongated member.

31. The minimally invasive fixation system of claim 30, wherein the articulating portion is selectively pivotable relative to the outer elongated member, the inner elongated member engaging a surface of the articulating portion to prevent pivoting of the articulating portion relative to the outer elongated member.

32. The minimally invasive fixation system of claim 30, wherein a biasing member is positioned between and operably associated with the inner and outer elongated members so that the inner elongated member is biased away from the articulating portion.

33. The minimally invasive fixation system of claim 29, wherein the articulating portion has an engagement device having a protrusion which selectively engages a recess in the rod, the articulating portion further including a biasing member configured to maintain the protrusion in the recess.

34. The minimally invasive fixation system of claim 33, the rod holder further comprising a shaft configured to move the protrusion out of the recess, wherein the articulating portion has a passageway through which the shaft moves when the articulating portion is substantially perpendicular to the elongated body.

35. The minimally invasive fixation system of claim 1, further comprising the bone anchor connected to the tissue protection portion.

36. The minimally invasive fixation system of claim 1, wherein the wall has a substantially curved shape.

37. The minimally invasive fixation system of claim 36, wherein the distal portion of the wall has a partially cylindrical shape.

38. The minimally invasive fixation system of claim 1, wherein the first distance is constant at the distal portion.

39. The minimally invasive fixation system of claim 1, wherein the wall also terminates at the proximal portion.

40. A method of placing a rod in first and second bone anchors, respectively, the method comprising:
    positioning a first tissue protection portion relative to the first bone anchor, the first tissue protection portion defining a first wall that has a proximal portion and a distal portion spaced from the proximal portion in a distal direction, the first wall defining a first axis that extends along the distal direction, the first wall revolving around the first axis to define a first passageway, wherein the proximal portion of the first wall does not revolve as far around the first axis as an entirety of the distal portion of the first wall revolves around the first axis, wherein no portion of the wall revolves completely around the axis;

moving the first tissue portion in the distal direction to a distal-most location relative to the first bone anchor so as to operatively couple the distal portion of the wall to the first bone anchor;

operatively coupling a second tissue protection portion to the second bone anchor, the second tissue protection portion defining a second wall;

aligning the first and second walls such that the first and second tissue protection portions define an opening between the first and second walls; and mounting the rod onto the first and second bone anchors.

41. The method of claim 40, further comprising fixing the rod with respect to the first and second bone anchors.

42. A minimally invasive fixation system comprising:
a first tissue protection portion configured to be mounted to a first bone anchor, the first tissue protection portion comprising a first wall having a first proximal portion and a first distal portion, the first wall defining a first axis that extends along a first direction from the first proximal portion to the first distal portion, the first wall extending around the first axis to define a first passageway, the first wall partially surrounds the first axis and terminates at an angular position having an angular length relative to the first axis that is less at the first proximal portion than at the first distal portion; and
a second tissue protection portion configured to be mounted to a second bone anchor, the second tissue protection portion comprising a second wall having a second proximal portion and a second distal portion, the second wall defining a second axis that extends along a second direction from the second proximal portion to the second distal portion, the second wall extending around the second axis to define a second passageway;
wherein the first and second tissue protection portions are configured to intermesh such that the first and second walls define an opening therebetween, the opening sized to receive a rod that is mounted on the first and second bone anchors.

43. The minimally invasive fixation system of claim 42, wherein the first proximal portion does not extend as far around the first axis as the first distal portion.

44. The minimally invasive fixation system of claim 42, wherein the second proximal portion does not extend as far around the second axis as the second distal portion.

45. The minimally invasive fixation system of claim 42, wherein the first wall comprises a first edge extending helically around the first axis from the proximal portion of the first wall toward the distal portion of the first wall.

46. The minimally invasive fixation system of claim 42, wherein the second wall comprises a second edge extending helically around the second axis from the second proximal portion toward the second distal portion.

47. A minimally invasive fixation system comprising:
a first tissue protection portion configured to be mounted to a first bone anchor, the first tissue protection portion comprising a first wall having a first proximal portion and a first distal portion, the first wall defining a first axis that extends along a first direction from the first proximal portion to the first distal portion, the first wall extending around the first axis to define a first passageway, the first wall defining a perimeter that extends around the first axis, wherein the perimeter at the first proximal portion extends around the first axis an angular amount less than at the first distal portion, wherein the first wall comprises a first edge extending helically around the first axis from the first proximal portion toward the first distal portion;
a second tissue protection portion configured to be mounted to a second bone anchor, the second tissue protection portion comprising a second wall, the second wall has a second proximal portion and a second distal portion, the second wall defines a second axis that extends along a second direction from the second proximal portion to the second distal portion, the second wall extends around the second axis to define a second passageway, and the second proximal portion does not extend as far around the second axis as the second distal portion.

48. The minimally invasive fixation system of claim 47, wherein the second wall comprises a second edge extending helically around the second axis in a direction from the second proximal portion toward the second distal portion.

49. The minimally invasive fixation system of claim 48, wherein the first and second edges are sized and configured to permit the first and second tissue protection portions to intermesh so that an opening is defined between the first and second walls to allow a rod to be inserted through the opening and mounted on the first and second bone anchors.

50. The minimally invasive fixation system of claim 47, further comprising the first bone anchor connected to the first tissue protection portion.

51. The minimally invasive fixation system of claim 50, further comprising the second bone anchor connected to the second tissue protection portion.

52. The minimally invasive fixation system of claim 47, further comprising a rod configured to be mounted onto the first and second bone anchors in an opening defined between the first and second walls.

* * * * *